United States Patent [19]

Bomalaski et al.

[11] Patent Number: 5,786,154
[45] Date of Patent: Jul. 28, 1998

[54] HUMAN PHOSPHOLIPASE ACTIVATING PROTEIN AND METHODS FOR DIAGNOSIS OF RHEUMATOID ARTHRITIS

[76] Inventors: John S. Bomalaski, 11 Chestnut La., Wayne, Pa. 19087; Mike A. Clark, 15 Wetmore Dr., Denville, N.J. 07835; Robert Shorr, 36 Overbrook Pkwy., Wynnewood, Pa. 19096

[21] Appl. No.: 465,421

[22] Filed: Jun. 5, 1995

Related U.S. Application Data

[62] Division of Ser. No. 236,410, May 2, 1994, Pat. No. 5,580,968, which is a division of Ser. No. 147,925, Nov. 4, 1993, Pat. No. 5,367,063, which is a division of Ser. No. 626,589, Dec. 6, 1990, Pat. No. 5,294,698.

[51] Int. Cl.$^6$ .................... G01N 33/543; G01N 33/564; G01N 33/573
[52] U.S. Cl. .................... 435/7.2; 435/7.4; 435/7.92; 435/7.94; 436/506; 436/509; 436/518
[58] Field of Search ............. 435/7.2, 7.4, 7.42, 435/7.94, 975; 436/506, 518, 509; 530/388.2, 389.1

[56] References Cited

U.S. PATENT DOCUMENTS

| | | |
|---|---|---|
| 4,916,056 | 4/1990 | Brown, III et al. .................... 435/7 |
| 5,153,166 | 10/1992 | Jain et al. .................... 502/402 |

FOREIGN PATENT DOCUMENTS

| | | |
|---|---|---|
| 356838 A | 7/1990 | European Pat. Off. . |
| 07-196698 A | 8/1995 | Japan . |
| 07-196699 A | 8/1995 | Japan . |

OTHER PUBLICATIONS

Pietsch, Borner and Tschopp, *TIBS*, 1993, 18, 292–293.

Clarke, et al., "Inhibition of phospholipase A$_2$ activation and arachidonic acid release by phospholipase A$_2$ activating protein (PLAP) antisense oligodeoxynucleotide," *The Faseb Journal*, Mar. 15, 1988, 2:4, Abstract No. 1436, A543.

Bomalaski, et al., "Inhibition of phospholipase A$_2$ activation and prostaglandin release by phospholipase A$_2$ activating protein (PLAP) antisense oligodeoxynucleotides," *Arthritis & Rheumatism*, Sep. 1990, 33:9 (supp) Abstract No. 151, S35.

Bomalaski, J.S. et al., "Monosodium Urate Crystals Stimulate Phospholipase A$_2$ Enzyme Activities and the Synthesis of a Phospholipase A$_2$–Activating Protein", *The J. of Immunol.* 1990, 145, 3391–3397.

Bomalaski et al., "Rheumatoid Arthritis Synovial Fluid Phospholipase A$_2$ Activating Protein (PLAP) Stimulates Human Neutrophil Degranulation and Superoxide Ion Production", *Agents & Actions* 1989, 27 (3/4), 425–427.

Bomalaski et al., "A Phospholipase A$_2$–Activating Protein (PLAP) Stimulates Human Neutrophil Aggregation & Release of Lysosomal Enzymes, Superoxide, and Eicosanoids", *J. of Immunol.* 1989, 142 (11), 3957–3962.

Clark et al., "Tumour Necrosis Factor (Cachectin) Induces Phospholipase A$_2$ Activating and Synthesis of a Phospholipase A$_2$–Activating Protein in Endothelial Cells", *Adv. Exp. Med. Biol.* 1990, 275, 125–144.

Clark et al., "Identification and Isolation of a Mammalian Protein Which is Antigenically and Functionally Related to the Phospholipase A$_2$ Stimulatory Peptide Melittin", *J. Biol. Chem.* 1987, 262(9), 4402–4406.

Green et al., "circulating Phospholipase A$_2$ Activity Associated with Sepsis and Septic Shock is Indistinguishable from that Associated with Rheumatoid Arthritis", *Inflammaizon* 1991, 15 (5), 355–367.

Heikkila, R. et al., "A c-myc Antisense Oligodeoxynucleotide Inhibits Entry into S Phase but not Progress from $G_0$ to $G_1$", *Nature* 1987, 328, 445–449.

Young et al., "Efficient Isolation of Genes by Using Antibody Probes", *PNAS USA* 1983, 80, 1194–1198.

Bomalaski et al, J. Lab. Clin. Med. 116 (6), 814–825, 1990.
Clark et al, Biochem J., 250, 125–132, 1988.
P. Tijssen, Practice and Theory of Enzyme Immunoassay, Elsevier Science Publishing Company, Inc., 1985, pp. 329–341.

*Primary Examiner*—David Saunders
*Attorney, Agent, or Firm*—Woodcock Washburn Kurtz Mackiewicz & Norris LLP

[57] ABSTRACT

The invention provides methods for detecting elevated levels of phospholipase A$_2$ activating protein in persons suspected of having rheumatoid arthritis to thereby indicate the presence of rheumatoid arthritis in the person comprising the steps of providing a sample of body fluid or tissue from said person; contacting the sample with an antibody specific for phospholipase A$_2$ activating protein such that the antibody binds with phospholipase A$_2$ activating protein in the sample; detecting the antibody thereby indicating the presence of phospholipase A$_2$ activating protein, whereby elevated levels of phospholipase A$_2$ activating protein in the sample as compared with levels found in persons not having rheumatoid arthritis indicates the presence of rheumatoid arthritis in the person. Kits and reagents for detecting rheumatoid arthritis are also provided.

1 Claim, 9 Drawing Sheets

Figure 1

| Peptide | No. of Amino acids | Sequence (NH$_2$ terminus to COOH terminus) |
|---|---|---|
| A | 14 | Lys-Val-Leu-Thr-Thr-Glu-Pro-Pro-Ile-Ile-Thr-Pro-Val-Arg |
| B | 10 | Lys-Val-Leu-Thr-Thr-Glu-Pro-Pro-Ile-Ile |
| C | 11 | Thr-Thr-Glu-Pro-Pro-Ile-Ile-Thr-Pro-Val-Arg |
| D | 9 | Lys-Val-Leu-Thr-Thr-Glu-Pro-Pro-Ile |
| E | 8 | Lys-Val-Leu-Thr-Thr-Glu-Pro-Pro |
| F | 6 | Lys-Val-Leu-Thr-Thr-Glu |
| G | 12 | Val-Leu-Thr-Thr-Glu-Pro-Pro-Ile-Ile-Thr-Pro-Val |
| H | 13 | Val-Leu-Thr-Thr-Glu-Pro-Pro-Ile-Ile-Thr-Pro-Val-Arg |
| I | 13 | Val-Leu-Thr-Thr-Glu-Pro-Pro-Ile-Ile-Thr-Pro-Val-Arg |
| 1 | 26 | PLAP amino acid 191 and amino acids in N-terminus direction |
| 2 | 26 | PLAP amino acid 192 and amino acids in N-terminus direction |
| 3 | 26 | PLAP amino acid 130 and amino acids in N-terminus direction |
| 4 | 26 | PLAP amino acid 132 and amino acids in carboxy-terminus direction |

FIGURE 2A

```
AACGACGGCCAGTGAAATTCCGCCGGCTCGGGCCTGTGGACGAGTCTCGC    -255
GCTGTGCCCGGGGGCGGCCGTCCGGATCCACGCTGGCCATGGCGAGCGCGC   -205
CTCCAGATACCGGCTGAGCTGCTCGCTACCGGCCACGAACTGGACGTGA     -155
GGGGCCTGGTGTGCTGCCTCTACCCGCCCGGAGCCTTTGTGTCTGTGTCCC   -105
GGGATCGACCACCCGCCCTCTGGGCTCCAGACAGTCCTAACAGGGCTTTA    -55
CAGAAATGCACTATATGAGCGGGCCACTCTAATTTTGTGTCTTATGTGT      45
      M   H   Y   M   S   G   H   S   N   F   V   S   Y   V   C
ATCATACCCTCAAGTGACATGACATATCCTCATGGACTGATTGCCACTGGAGG  95
 I   I   P   S   S   D   I   Y   P   H   G   L   I   A   T   G   G
AAATGACCACCAATATTTGCATTTTCTCGCTGGACAGTCCAATGCCACTTT   145
 N   D   H   N   I   C   I   F   S   L   D   S   P   M   P   L   Y
ATATTTTAAAGGGTCACAAAGATACTGTTTGTAGTCTTTCTCTGAAAA      195
 I   L   K   G   H   K   D   T   V   C   S   L   S   S   G   K
TTTGGGACATTACTTAGTGGCTCATGGGACACCACTGCTAAAGTCTGGCT    245
 F   G   T   L   L   S   G   S   W   D   T   T   A   K   V   W   L
GAATGACAAATGCATGATGACATTACAGGGTCATACAGCCGCAGTATGG     295
 N   D   K   C   M   M   T   L   Q   G   H   T   A   A   V   W   A
CAGTAAAGATTTTACCTGAACAGGGCTTAATGCTAACTGGATCAGCAGAC    345
 V   K   I   L   P   E   Q   G   L   M   L   T   G   S   A   D
AAGACCATTAAACTATGGAAGGCTGGAAGATGTGAGAGGACTTTTTTAGG    395
 K   T   I   K   L   W   K   A   G   R   C   E   R   T   F   L   G
```

FIGURE 2B

```
GCATGAAGACTGTGTAAGAGGCTTGGCAATCTTGAGTGAGACAGAATTC     445
 H  E  D  C  V  R  G  L  A  I  L  S  E  T  E  F  L
TTTCCTGTGCAAACGATGCTAGTATTAGAAGGTGGCAGATCACTGGCGAG     495
  S  C  A  N  D  A  S  I  R  R  W  Q  I  T  G  E
TGTCTGGAAGTATACTTTGGACATACAAATTATATTTATAGCATATCTGT     545
 C  L  E  V  Y  F  G  H  T  N  Y  I  Y  S  I  S  V
CTTTCCAAACTCCAAAGATTTTGTGACCACTGCAGAAGACAGATCTCTAA     595
 F  P  N  S  K  D  F  V  T  T  A  E  D  R  S  L  R
GAATATGGAAACATGGTGAATGCGCCCAAACAATCCGACTTCCAGCTCAG     645
  I  W  K  H  G  E  C  A  Q  T  I  R  L  P  A  Q
TCTATATGGTGTTGCTGCTACTGGAAAATGGTGACATTGTGGTTGGTGC      695
 S  I  W  C  C  V  L  E  N  G  D  I  V  V  G  A
GAGTGATGGTATTATTAGGGTGTTTACAGAGTCAGAGGAGCGGACAGCAA     745
  S  D  G  I  I  R  V  F  T  E  S  E  E  R  T  A  S
GTGCTGAGGAATCAAAGCTTCTCTCTCGAGAGAGTCCGTTGATAGCT       795
 A  E  E  I  K  A  S  L  S  R  E  S  P  L  I  A
```

FIGURE 2C

```
AAGGTTTGACCACTGAACCCCCTATAATTACGCCCTGTCCGAAGGACCCT    845
 K  V  L  T  T  E  P  P  I  I  T  P  V  R  R  T  L
CCCTTGTAGAGTCACTCGGTCCATGTCTCTTCCTGTCTGAGCAGATTAG     895
 P  C  R  V  T  R  S  M  I  S  S  C  L  S  R  L  V
TCTCTACCTCTCTCTCCAACTTCGGATAGTCACCTCACAATCACTGCCCTC   945
 S  T  S  L  S  T  S  D  S  H  L  T  I  T  A  L
CACCTATTTTTAACCACTACAACAACCGAGTAGACCACGATTAGTCGTTT    995
 H  L  F  L  T  T  T  T  E  *
GTAGACCTTTCAAAATATACTTCCCTTTCTTAAACTAATACAAAAGAGT    1045
TAGCTACACTTACTTCCACCTGGTAGCATATTTAATGGTATATTACAGTC   1095
ACTGCTAGGGACCGATCAACGTATGTTGAAGAACGTCTTTTTACTAAACT   1145
TAGGGTACAAAGACCTAGTCCACCGATTTAAATAATAACTATTGTGTTTT   1195
CCAGTTTGTGACCCTGAACCCTTATGGTCAAAAAGTCTAGGCAAATGTCC   1245
ACCACCAGCGATACAAGGTCCTGAAGTCCTGGAAGGTTGTGTACGTTCT    1295
GTCGTCTAGGAAAGTGTCCACGACCCGCAATGTACGGTCCAAGACGTCCA   1345
TACCTGTGGTGGTACTGACCTCAACTAGGTAAATGTCCCTTGTCACGGAT   1395
```

FIGURE 2D

```
GGCTAGTCGACGTAGATTTTGTCACTTGTAAATAAAGGGGTTTTTTCTTC    1445
GAGAATGGAAACTGGTTTGTTTGGGATGTGTTTATAATCCTTTTGACTTC    1495
CTTGAATTACCTTGACGTGGACTTCTCTTCTCGATTGACTTCTGCTGAA     1545
TCATGAAGAACTTTCTATGACAGGACTAAACATTATTAAGGAGTCTTT      1595
TCGGTTGCGCGGTCGTTGAAGTCTAAAACACCTTTCGATAGTTGACCGGA    1645
CTTCTGTAACAGAAGGACGTGAACTGTAAGAAGCGGATAGCTAATTCGT     1695
AGGGTTACACTTACTCTTAAAGACGTTACTTTTTCCTCTGGTCAAGTCGT    1745
CGGTAGAATAGTTGGAAGACTTGGGGTTTCCTTTCGTCGTTTGGTCGAC     1795
GAACGAGAATCCTGAAAACGTAACGAAACAATCAGTCCGTCCTGTTTT      1845
CGAGTACTACAGGGTCTCCTCAGTGACTACAGTGTACGTTATCTTGATTT    1895
TAGGCCCTCATTATTCTTGTAAGTATAACGAGACCGATGTAACTGGAACT    1945
TGATAAGACAAACAAAGGTATTTCTGGTATTGTAACTTCCCTTTCGAGTT    1995
ACGGAGAGTCATTAATCGTGTTAGAACACCGAGAACCCTGAATAGTCACG    2045
GTGCAAATCTGAGGAACACCGAGAACCCTGTGAATAGTCACTACTAAGTT    2095
TACGATATGTTAATCGGTTTAGAAATCCACAACTAAGAGTTTATTTTTC     2145
ATACAGAGCATAGTCTCGGTCGATTCACTTCACTTACGACATCTGAACA     2195
GAATGTAAACGACATCGTCACCCCTTTTCTGCGACTCCCCAAAAGAAAAA    2245
AACAAAACAAAAACAAAAACAAAAAAAGGTGTAAAATGTACTGACTAACGTC  2295
TAC                                                   2298
```

FIGURE 6

```
Melittin   GlyIleGlyAlaValLeuLysValLeuThrThrGlyLeuProAla
PLAP       GluSerProLeuIleAlaLysValLeuThrThrGlu - ProPro Melittin   LeuIleSerTrpIleLysArgLysArgGlnGln
PLAP       IleIleThrProValArgArg
```

1

HUMAN PHOSPHOLIPASE ACTIVATING PROTEIN AND METHODS FOR DIAGNOSIS OF RHEUMATOID ARTHRITIS

This is a division of application Ser. No. 08/236,410, filed May 2, 1994 and now U.S. Pat. No. 5,580,968, which is a division of application Ser. No. 08/147,925, filed Nov. 4, 1993 and now U.S. Pat. No. 5,367,063, which is a division of application Ser. No. 07/626,589, filed Dec. 6, 1990 and now U.S. Pat. No. 5,294,698.

FIELD OF THE INVENTION

The present invention relates to the field of methods for diagnosing rheumatoid arthritis. More particularly the present invention relates to methods for diagnosing rheumatoid arthritis using immunoassays.

BACKGROUND OF THE INVENTION

Rheumatoid arthritis is the best known form of arthritic disease, affecting millions of patients worldwide. It is characterized by a progressive inflammation of joints and internal organs by immunocompetent cells and destructin of articular cartilage resulting in progressive morbidity and death. Prostaglandins and related eicosanoids are thought to be important mediators of these immune and inflammatory responses. Increased quantities of eicosanoids are produced by rheumatoid synovium in both organ and cell culture and are found in elevated levels in rheumatoid synovial fluid and from peripheral blood cells of affected patients. Clinical evidence suggests that early diagnosis and intervention with cytotoxic and immunomodulatory agents is essential to altering the course of the disease.

Phospholipase $A_2$ (PLA$_2$) is a lipolytic enzyme which hydrolyzes the 2-acyl fatty acid ester of glycerophospholipids, thus releasing arachidonic acid. Arachidonic acid has been shown to be converted into a number of biologically active compounds known as eicosanoids. PLA$_2$ activity has been shown to be ubiquitous and to reside in several different gene products. Both membrane bound and soluble forms of the enzyme have been described. Extracellular secretion of soluble PLA$_2$ was first described in 1980. Circulating PLA$_2$ was implicated in endotoxin shock and has since been implicated in acute and chronic inflammatory reactions.

Currently rheumatoid arthritis is diagnosed on the basis of the patient's physical presentation and a limited number of laboratory tests. Most of these tests indicate a generalized inflammatory state and diagnosis is only reinforced on the basis of cumulative results. Of the laboratory tests designed to be more specific, the presence of rheumatoid factor has been shown to correlate with approximately 75% of bonafide rheumatoid arthritis cases and attempts have been made to establish rheumatoid factor as a distinguishing criteria from other inflammatory diseases. Incorrect diagnoses of rheumatoid disease, based upon rheumatoid factor, however, do occur with hepatitis, sarcoidosis and infections, as well as other inflammatory joint diseases such as Reiters syndrome. In addition at least 5% of disease free individuals over age 65 test positive for the presence of rheumatoid factor. Further, elevated or depressed levels do not correspond well with flare-ups or remissions in rheumatoid disease. Clearly, rheumatoid factor is neither sensitive nor specific for the diagnosis or prognosis of rheumatoid arthritis and other more sensitive and specific methods for diagnosing and following the course of the disease are needed.

It is thus an object of the invention to provide such methods. It is also an object of the invention to provide test kits and reagents for diagnosing or following the course of rheumatoid arthritis in persons having the disease. It is a further object of the invention to provide nucleic acid sequences, polypeptides and antibodies useful in diagnosing or following the course of rheumatoid arthritis. It is yet another object of the invention to provide antisense oligonucleotides and other substances useful in the treatment of rheumatoid arthritis.

SUMMARY OF THE INVENTION

The present invention provides a novel human phospholipase $A_2$ activating protein (PLAP). The novel phospholipase $A_2$ activating protein of the invention was isolated from synovial fluid of patients presenting with bona fide rheumatoid arthritis. The invention also provides methods, kits, and reagents for diagnosing and following the course of rheumatoid arthritis. The invention further provides a nucleic acid sequence coding for PLAP.

The correlation of elevated levels of this protein in rheumatoid arthritic patients over levels found in the synovial fluid of patients with osteoarthritis (degenerative arthritis), the prototypical inflammatory arthritic disease, is greater than 87%. In addition levels of the protein are likely to correspond to remission or flare-ups of the disease. In contrast patients with other forms of inflammatory joint disease such as Reiter's syndrome, and pseudogout or ankylosing spondylitis fail to show elevated PLAP levels. Assays for PLAP are likely to be unaffected by hepatitis, sarcoidosis, or most infections. Thus, levels of PLAP in synovial fluid and possibly serum can be used for the diagnosis and monitoring of rheumatoid arthritis without those difficulties and uncertainties associated with rheumatoid factor.

This invention is more particularly pointed out in the appended claims and is described in its preferred embodiments in the following description.

BRIEF DESCRIPTION OF THE DRAWINGS

FIG. 1 shows examples of PLAP fragments tested for PLA$_2$ stimulating activity. The PLAP fragments shown in FIG. 1 are represented as follows: A—SEQ ID NO: 8; B—SEQ ID NO: 9; C—SEQ ID NO: 10; D—SEQ ID NO: 11; E—SEQ ID NO: 12; F—SEQ ID NO: 13; G—SEQ ID NO: 14; H—SEQ ID NO: 15; I—SEQ ID NO: 16; 1—SEQ ID NO: 4; 2—SEQ ID NO: 5; 3—SEQ ID NO: 6, 4—SEQ ID NO: 7.

FIG. 2 shows the sequence of PLAP cDNA (SEQ ID NO: 1). The predicted amino acid sequence of the largest open reading frame is also shown (SEQ ID NO: 2). The predicted amino acid sequence begins a 1 (underlined ATG) The region having the greatest homology with melittin is highlighted and underlined. The complimentary antisense DNA used in Tables 7, 8, and 9 was synthesized using the region encoded between the two arrows which begins at the codon after ATG, methionine which is 1.

FIG. 6 shows a comparison of the amino acid sequence of mellitin (SEQ ID NO: 3) and amino acids 260–280 of PLAP (SEQ ID NO: 2, amino acids 260–180).

DETAILED DESCRIPTION OF THE INVENTION

Figure 3:
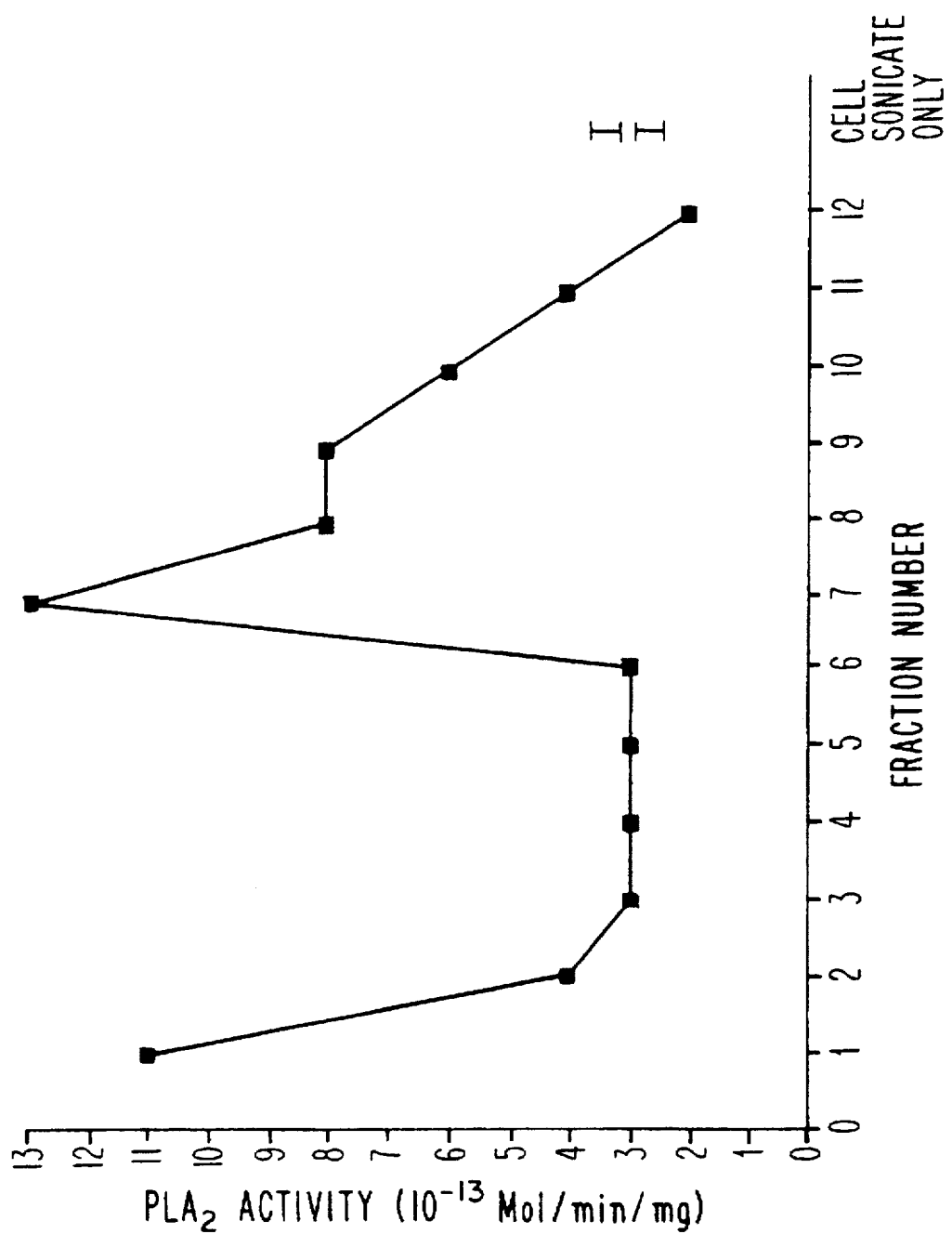
FIG. 3 shows a graph of the PLA$_2$ activity of fractions of PLAP collected from a anti-melittin affinity chromatography column during purification of PLAP from human synovial fluid.

The present invention provides a novel human phospholipase $A_2$ activating protein (PLAP) useful in assays for diagnosing and following the course of rheumatoid arthritis.

The invention also provides a method for detecting elevated levels of phospholipase $A_2$ activating protein in persons suspected of having rheumatoid arthritis to thereby indicate the presence of rheumatoid arthritis in the person comprising the steps of providing a sample of body fluid or tissue from said person; contacting said sample with an antibody specific for phospholipase $A_2$ activating protein such that said antibody binds with phospholipase $A_2$ activating protein in the sample; and detecting the antibody thereby indicating the presence of phospholipase $A_2$ activating protein, whereby elevated levels of phospholipase $A_2$ activating protein in the sample as compared with levels found in persons not having rheumatoid arthritis indicates the presence of rheumatoid arthritis in the person.

Another embodiment of the invention provides substantially purified nucleic acid sequences coding for the phospholipase $A_2$ activating protein. A nucleic acid sequence coding for phospholipase $A_2$ activating protein isolated from bovine cells is shown in FIG. 2. The predicted amino acid sequence of PLAP is also shown.

A further embodiment of the invention provides a method for purifying human phospholipase $A_2$ activating protein from body fluid or tissue comprising the steps of a) contacting the body fluid or tissue with anti-melittin or anti-phospholipase $A_2$ activating protein antibodies bound to a solid support wherein phospholipase $A_2$ activating protein in the body fluid or tissue binds with anti-melittin or anti-phospholipase $A_2$ activating protein antibodies; b) eluting bound phospholipase $A_2$ activating protein from said solid support; c) passing eluted phospholipase $A_2$ activating protein from step b through a size exclusion column; and d) collecting purified phospholipase $A_2$ activating protein. A preferred solid support is silica. The eluting step is preferably performed with sodium acetate buffer.

Another embodiment of the invention provides a method of detecting phospholipase $A_2$ activating protein in a mammalian body fluid or tissue comprising the steps of contacting a sample of the body fluid with an antibody specific for phospholipase $A_2$ activating protein whereby the antibody binds to phospholipase $A_2$ activating protein in the body fluid or tissue, and detecting the antibody thereby indicating the presence of phospholipase $A_2$ activating protein in the body fluid or tissue. The detecting step may further comprise contacting bound antibody specific for phospholipase $A_2$ activating protein with a detectably labeled antibody bindable with the bound antibody; and detecting the detectable label. In a preferred embodiment the detectable label is peroxidase and the detecting step contacting the peroxidase with O-phenylenediamine substrate and determining optical density of the substrate product.

The invention also provides reagents and kits for detecting rheumatoid arthritis and phospholipase $A_2$ activating protein in mammalian body fluid or tissue. The reagents of the invention comprise comprising an antibody specific for phospholipase $A_2$ activating protein and a carrier or diluent. Kits of the invention comprise a solid surface having an antibody specific for phospholipase $A_2$ activating protein-bound thereon, at least one reagent comprising an antibody specific for phospholipase $A_2$ activating protein and a carrier or diluent; and means for detecting the antibody.

The invention further provides a method of inhibiting the synthesis of phospholipase $A_2$ activating protein in mammalian cells comprising the steps of contacting a mammalian cell with antisense nucleic acid sequence coding for a phospholipase $A_2$ activating protein synthesis inhibiting sequence of phospholipase $A_2$ activating protein whereby said antisense nucleic acid sequence inhibits synthesis of phospholipase $A_2$ activating protein. The antisense sequence may be prepared as DNA or RNA.

A further embodiment of the invention provides a method of treating mammalian, preferably human, rheumatoid arthritis comprising administering to a mammal a PLAP synthesis inhibiting amount of an antisense nucleic acid sequence coding for at least a portion of PLAP.

The destructive effects of rheumatoid arthritis on joints is associated with enhanced production of eicosanoids derived from arachidonic acid. Increased quantities of eicosanoids are produced by rheumatoid synovium in both organ and cell culture and are found in elevated levels in rheumatoid synovial fluid and from peripheral blood cells of affected patients.

At the present time, persons having rheumatoid arthritis are treated with non-steroidal anti-inflammatory drugs which inhibit the production of eicosanoids. The rate limiting step in eicosanoid biosynthesis is the release of arachidonic acid from membrane phospholipids by phospholipase enzymes, so that activation of arachidonic acid release by PLAP would effectively increase eicosanoid synthesis by making available its biosynthetic precursor. PLAP thus appears to be an important mediator of the effects of rheumatoid arthritis.

Applicants have discovered that PLAP induces eicosanoid release and stimulation of joint inflammation. To demonstrate PLAP induction of eicosanoid release, normal human peripheral blood monocytes preloaded with labelled arachidonic acid were stimulated with PLAP. A significant release of arachidonic acid metabolites was observed. Radioimmunoassay for specific metabolites of unlabelled cells showed prostaglandin $E_2$ as the major metabolite released. PLAP was also shown to stimulate release of leukotriene $B_4$ and prostaglandin $E_2$.

PLAP stimulation of an inflammatory arthritogenic response was examined by injection of purified PLAP into rabbit knee joints. PLAP was found to have a dose-response relationship in mediating an inflammatory arthropathy with cellular infiltration and joint destruction.

To determine the cellular source of PLAP found in human joints, metacarpophalangeal and knee joint specimens were obtained from patients with rheumatoid arthritis or osteoarthritis and immunohistochemical staining with anti-PLAP antibodies performed. All 6 rheumatoid arthritic patients tested displayed intense staining. No staining was observed with the specimens obtained from osteoarthritic patients. Microscopic examination revealed heavy staining of synovial monocytes, macrophages, and multinucleated giant cells with some additional staining of vascular smooth muscle and endothelial cells. Similar results were observed in rheumatoid nodules. Osteoarthritic synovium revealed no PLAP staining even under microscopic examination. No staining was observed in either specimen type with pre-immune antisera.

In order to quantitate the presence of PLAP as a function of the presence and stage of rheumatoid arthritic disease ELISA assays were performed on a broad spectrum of synovial fluid samples drawn from rheumatoid arthritic patients, normal healthy volunteers, and patients with other form of arthritis or joint disease. Specimens from patients with rheumatoid arthritis showed an average 4.3-fold increase in PLAP levels over healthy synovial fluid or fluid from patients with osteoarthritis. Within the detection limits of the assay 87% of rheumatoid arthritic patient synovial fluid showed elevated PLAP levels. Elevated levels of PLAP were detected in rheumatoid arthritic patients and increased levels of the activating protein were associated with severity of the disease ($p<0.05$).

Applicants have found that PLAP has a biochemical affinity for a subset of $PLA_2$ activity selective for lipolysis of phosphatidylcholine, possibly like melittin preferring arachidonic acid as the sn-2 fatty acid. Indeed the specificity of PLAP is particularly relevant to rheumatoid arthritis since phosphatidylcholine and lysophosphatidylcholine are the major phospholipids in inflammatory synovium and synovial fluid aspirated from rheumatoid arthritic patients.

The extensive tissue necrosis and hemorrhage associated with injection of 100000 PLAP units is similar to that observed in other experimental systems with the injection of melittin (Kurihara Cell Tissue Res. (1986)). Since over 400000 units of PLAP could be recovered from as little as 10 ml of synovial fluid from rheumatoid arthritic patients it is clear that pathophysiologic concentrations of PLAP may play a key role in mediating the disease.

Purified human PLAP has an apparent molecular mass of about 28,000 as determined by SDS gel electrophoresis. PLAP may be purified from human synovial fluid or other human fluid or tissue containing the protein by affinity chromatography using immobilized anti-mellitin antibodies or antibodies specific for PLAP, followed by high pressure liquid chromatography (HPLC) using a size exclusion gel, preferably a silica gel, or any other conventional method, or combination of methods for isolating proteins that results in substantially purified PLAP. Preferred methods for isolating PLAP from human synovial fluid are described in detail in the Examples. PLAP is preferably isolated from synovial joint fluid of persons having rheumatoid arthritis, as the level of PLAP is higher in these persons. However, synovial fluid from persons not having rheumatoid arthritis is also suitable, although larger quantities of synovial fluid may be necessary due to the comparatively lower amount of PLAP in the synovial fluid of persons not having rheumatoid arthritis. Methods for affinity chromatography, high pressure liquid chromatography and other methods useful for isolating proteins may be found in the scientific literature and standard texts in the field such as Scopes, R. K., *Protein Purification, Principles and Practice*, second edition, Springer-Verlag, New York, N.Y., 1987.

In addition to purification from natural sources, PLAP may also be obtained using recombinant DNA techniques. A nucleic acid sequence coding for PLAP may be obtained from mammalian cells by amplification of nucleic acid using nucleic acid primers having the sequence of the beginning or end portions of PLAP (human or from other species) and polymerase chain reaction procedures, followed by insertion of the amplified nucleic acid into a cloning vector such as lambda gt11, and subsequently inserting the amplified sequence into an expression vector and host cell, and screening for the sequence coding for PLAP using antibodies specific for PLAP. A nucleic acid sequence coding for PLAP may also be obtained by screening a DNA library (genomic or cDNA) from the cells of a mammal for the sequence, or for shorter sequences that taken together code for the entire sequence of PLAP, as described in Sambrook et al., *Molecular Cloning, A Laboratory Manual*, second edition, Cold Spring Harbor Laboratory Press, Cold spring Harbor, N.Y., 1989. A preferred method for isolating a nucleic acid sequence coding for PLAP is described in the Examples. A preferred cell line for isolation of PLAP is BC3H1, a murine smooth muscle-like brain tumor cell line obtainable from the American Type Culture Collection (accession number CRL 1443). As an alternative to the BC3H1 cell line, other types of mammalian cells and cell lines such as human cells and cell lines may be used for isolation of a nucleic acid sequence coding for PLAP. Nucleic acid coding for PLAP isolated from any source is within the scope of the invention, and is suitable for the purposes of the invention as described herein.

Fragments or subportions of PLAP having immunogenic activity or $PLA_2$ stimulating activity are also within the scope of the invention. Fragments of PLAP leaving immunogenic activity includes fragments of PLAP of any size that are capable of serving as antigen for production of antibodies specific for PLAP, whether or not conjugated to a carrier protein. As used herein $PLA_2$ activating activity, $PLA_2$ stimulating activity and similar terms are intended to refer to increasing $PLA_2$ activity to levels above the level of endogenous $PLA_2$ activity found in controls in the $PLA_2$ activating assays described herein. Thus a $PLA_2$ stimulating or activating portion of PLAP is one that stimulates $PLA_2$ activity to levels above those found endogenously.

Fragments of PLAP include polypeptides or peptides having fewer amino acids than PLAP. Preferred fragments of PLAP are from about six to about 30 amino acids in length, more preferably about 26 amino acids in length. Fragments of PLAP are preferably selected such that the amino acid sequence of the fragment contains at least a part of the sequence homologous with melittin. Melittin is a low molecular weight peptide containing 26 amino acids found in bee venom that has phospholipase activating activity.

The amino acid sequence of PLAP (SEQ ID NO: 2) shows significant sequence homology with melittin (SEQ ID NO: 3) in the regions around amino acids 131 and 132, amino acids 191–193, and amino acids 260 through 280. The amino acid sequence of melittin and the predicted amino acid sequence of PLAP were compared using the Wisconsin database software (GCG). A comparison of the amino acid sequence of melittin and amino acids 260–280 of PLAP is shown in FIG. 6. At the present time fragments of PLAP selected to contain at least a portion of the amino acids in one of these regions is preferred, more preferably the fragment contains at least half to all of the amino acids in one of these regions. Fragments may be selected by using one of the aforementioned homologous regions as a starting point and proceeding either towards the animo terminus or the carboxy terminus of PLAP for the desired number of amino acids, and constructing a fragment or peptide heaving the corresponding amino acid sequence. Examples of peptides of varying length may be found in FIG. 1. These peptides were selected from the regions of PLAP having homology with mellitin. Applicants have found that fragments (or peptides) selected from this area have $PLA_2$ stimulating activity as shown in Table 1. Also at the present time, preferred fragments are those having greatest amounts of $PLA_2$ stimulating activity. Fragments of PLAP selected outside the aforementioned areas that have $PLA_2$ stimulating activity are also within the scope of the invention. Peptides 26 amino acids in length having the sequence of the amino or carboxy terminus of PLAP have been tested, but were not found to have $PLA_2$ stimulating activity.

Fragments of PLAP may be prepared by any method for preparing peptides including chemical synthesis, recombinant DNA techniques, and degradation of PLAP. Chemical synthesis of the fragments or peptides is presently preferred for convenience of preparation. The fragments or peptides may be synthesized by any convenient method for synthesizing peptides or proteins.

TABLE 1

| Peptide | SEQ ID NO: | Phospholipase A₂ activating activity |
|---|---|---|
| A | 8 | ++ |
| D | 11 | − |
| F | — | ± |
| G | 14 | ± |
| 1 | 4 | + |
| 2 | 5 | + |
| 3 | 6 | + |
| 4 | 7 | + |

++ indicates PLA$_2$ stimulating activity approximately 5 times greater than controls; + indicates 2–5 fold stimulation of PLA$_2$ activity when compared to controls; ± and ± indicate inconclusive results for PLA$_2$ stimulating activity; − indicates no PLA$_2$ stimulating activity.

A nucleic acid sequence coding for PLAP isolated from the murine BC3H1 cell line as described herein is shown in FIG. 2 (SEQ ID NO: 1). Fragments, subsequences, additions and deletions of bases from the sequence that code for PLAP fragments, portions, or derivatives capable of serving as antigen for production of antibodies specific for PLAP, whether conjugated to a carrier protein or not, or that code for a portion of PLAP having PLA$_2$ stimulating activity are also within the scope of the invention.

For diagnosing and following the course of rheumatoid arthritis, synovial fluid is removed from at least one affected joint of a patient suspected of having rheumatoid arthritis. The synovial fluid is then tested to detect the presence of elevated levels of PLAP which would signify rheumatoid arthritis. The synovial fluid is tested using immunoassays described herein in another embodiment of the invention. The immunoassays of the invention may be used in combination with other symptoms of the patient to diagnose the disease. Generally the immunoassays will be performed by physicians or other trained medical personnel after a physician has examined the person and suspects that the person has rheumatoid arthritis based on the physical symptoms to the person. The symptoms of rheumatoid arthritis are well-known to physicians. Once the physician suspects the person has rheumatoid arthritis, the immunoassays of the invention may be performed to rule in or rule out the presence of the disease in the person. The physical manifestations of rheumatoid arthritis are sometimes difficult to differentiate from other diseases, such as osteoarthritis, pseudogout, and seronegative spondyloarthropathy. The immunoassays of the invention will allow the physician to correctly diagnose the disease, and prescribe appropriate treatment. Thus the immunoassays of the invention are also useful for ruling out the presence of rheumatoid arthritis in persons suspected of having the disease.

Since normal human, and other mammalian synovial fluid and tissues contain PLAP, it may be necessary, in order to determine elevated levels of PLAP to obtain baseline or background levels of PLAP, and to calibrate a particular embodiment of the immunoassays of the invention to take into account the presence of PLAP in healthy persons not having rheumatoid arthritis. For example, the concentration of PLAP in a sample of persons not having rheumatoid arthritis would be determined and used to compare with the amount of PLAP found in a sample from a person suspected of having rheumatoid arthritis. If the amount of PLAP in the sample from the person suspected of having rheumatoid arthritis is greater than the baseline or background levels found in the healthy persons, the increased amount would indicate the presence of rheumatoid arthritis in the person. Similarly, the value for elevated levels of PLAP may be calibrated by testing persons known to have rheumatoid arthritis to determine elevated levels of PLAP for a particular embodiment of the immunoassays of the invention. For example, commonly used detectable labels such as enzymes use different calorimetric substrates that are detected by spectroscopy at different wavelengths. Results are typically read as optical density at a certain wavelength. Thus a baseline amount of PLAP would be established as a the optical density present when the synovial fluid of healthy persons is tested. Elevated levels would be established in a similar manner. Once baseline levels and elevated levels are established, the significance of a patient's result will be routine to establish. The level of PLAP in a sample from a person suspected of having rheumatoid arthritis is determined using an immunoassay of the invention, and the result is compared with the baseline, and possibly elevated levels for the immunoassay. If the sample contains elevated levels of PLAP, the person very likely has rheumatoid arthritis. If the level falls between the elevated level and the baseline level, a diagnosis of rheumatoid arthritis is not as likely. In addition to calibration for a particular type of immunoassay, it may also be necessary to establish baseline and elevated levels of PLAP for a particular type of tissue. All such manipulations are within the scope of one skilled in the art.

Synovial fluids from persons having rheumatoid arthritis consistently contain very high levels of PLA$_2$ activity when compared to synovial fluid from normal patient joints or even the serum from rheumatoid arthritic patients. In contrast synovial fluid from inflamed osteoarthritic joints shows only slightly elevated levels of phospholipase activity.

The immunoassays of the invention may also be used to follow the course of rheumatoid arthritis. Since, rheumatoid arthritis is a long term chronic disease for which there is at the present time no cure, it would be useful to have assays to determine the effectiveness of therapeutic agents used in treating the disease, and possibly in determining flare-ups or remissions of the symptoms. The immunoassays of the invention may accordingly be performed at predetermined intervals or when desired by the physician or patient to determine the level of PLAP in the synovial fluid of the person having the disease. The level of PLAP in the synovial fluid should give an indication of the state of the disease.

Synovial fluid or other body fluid or tissue may contain components that could interfere with the performance of the immunoassays of the invention and which may need to be removed prior to use. Synovial fluid is preferably centrifuged prior to use in the immunoassay, and the clarified fluid is used. Similarly, when body tissues are used, the tissues are preferably ground into small pieces, such as in a blender, then centrifuged to separate the pieces of tissue, and supernatant used in the immunoassays of the invention.

The immunoassays of the invention may be performed using a conventional immunoassay format such as antibody capture, antigen capture, or two-antibody sandwich assays. Immunoassay formats may be found in standard texts such as Harlow and Lane, *Antibodies, A Laboratory Manual*, Cold Spring Harbor Laboratory, Cold Spring Harbor, N.Y., 1988. In a preferred immunoassay, synovial fluid suspected of containing PLAP is deposited in a multi-well microtiter plate. Antibodies specific for PLAP are then contacted with the components of the synovial fluid, including PLAP if present. Bound antibody is then contacted with second a detectably labeled antibody capable of binding with the antibody specific for PLAP, and the detectable label is detected, thereby signifying the presence of PLAP in the synovial fluid. Alternatively, anti-PLAP antibodies could be deposited in wells of a microtiter plate and synovial fluid contacted with the deposited antibodies where PLAP in the synovial fluid would bind to the deposited antibodies. Bound PLAP could then be detected by binding a detectably labeled anti-PLAP antibody to the bound PLAP, and subsequently detecting the detectable label. Other immunoassays may be readily designed to detect PLAP by reference to standard texts in the field referred to above. As used herein, the term antibody is intended to mean antibodies, and any fragments or portions of antibodies that are capable of binding to PLAP.

Immunoassays may also be used to detect the presence of PLAP in tissue, such as joint tissue, in situ. Tissue specimens may obtained and prepared according to conventional methods for preparing tissues. Antibodies specific for PLAP are then contacted with the prepared tissue where the antibodies will bind to PLAP in the tissue. Bound antibodies are then detected.

Suitable detectable labels for use in the immunoassays of the invention include enzymes such as horseradish peroxidase and alkaline phosphatase, radiolabels such as $^{123}$I and $^{32}$P, and biotin systems, latex particles, electron dense materials such as ferritin, light scattering materials such as gold. Suitable detectable labels for use in the immunoassays of the invention may be found in Harlow and Lane, *Antibodies, A Laboratory Manual*, supra and other standard texts in the field. Suitable methods for detecting the detectable label include scintillation counting, autoradiography, fluorescence measurement, calorimetric measurement, or light emission measurement.

Thus, the labeling may comprise a radiolabel (e.g. $^{14}$C, $^{32}$P, $^{3}$H, and the like), an enzyme (e.g., peroxidase, alkaline or acid phosphatase, and the like), a bacterial label, a fluorescent label, an antibody (which may be used in a double antibody system), an antigen (to be used with a labeled antibody), a small molecule such as biotin (to be used with an avidin, streptavidin, or antibiotin system), a latex particle (to be used in a buoyancy or latex agglutination system), an electron dense compound such as ferritin (to be used with electron microscopy), or a light scattering particle such as colloidal gold, or any combinations or permutations of the foregoing.

For ease in performance of the immunoassays of the invention, the immunoassays may be provided in a kit form. The kits of the invention comprise an solid surface, such as a multi-well titer plate, nitrocellulose strip, tissue culture plates or other apparatus for containing or binding PLAP or anti-PLAP antibodies, and one or more reagents for detecting PLAP. The kits may also comprise one or more reagents for standards or controls. For example, in a preferred embodiment, the kits may comprise a multi-well plate for depositing the synovial fluid sample, a reagent comprising antibody specific for PLAP, a reagent comprising enzyme-labeled antibody bindable with the antibody specific for PLAP, and a reagent comprising substrate for the enzyme. The kits of the invention will vary according to the format of the immunoassay used to detect PLAP. If the immunoassay is to be performed in a liquid, the kits may comprise one or more containers for performing the assay, and one or more reagents for detecting PLAP. The reagents of the invention comprise antibodies specific for PLAP or a PLA$_2$ stimulating portion thereof and a carrier or diluent. Suitable carriers or diluents include water, and saline, or other buffer. The reagents may also comprise preservatives or stabilizers.

The reagents of the invention may be supplied without the carrier or diluent, such as would be the case if the reagent were freeze-dried. A suitable amount of the carrier or diluent would then be added by prior to using the reagent.

Polyclonal and monoclonal antibodies specific for PLAP or fragments of PLAP may be prepared by standard techniques in the field such as may be found in Harlow and Lane, *Antibodies, A Laboratory Manual*, supra and other standard texts in the field. To prepare polyclonal antibodies, purified PLAP, PLAP produced by recombinant DNA techniques (rPLAP) or fragments of purified PLAP or rPLAP are injected into an animal such as a rabbit, or mouse. Antibodies produced by the animal in response to PLAP or fragment are then purified from the serum of the animal. Since some of the fragments of purified PLAP or rPLAP may not be large enough to produce a strong immune response in the animal, they may be conjugated to a carrier protein such as keyhole limpet hemocyanin or bovine serum albumin prior to injection into the animal. Monoclonal antibodies may be produced using the method of Kohler and Milstein, Nature 256: 495–497 (1975), or as described in standard texts in the field such as Harlow and Lane, *Antibodies, Laboratory Manual*, supra.

EXPERIMENTAL

Materials and Methods

Radioactive materials were purchased from New England Nuclear (Boston, Mass.). Tissue culture media and serum were from Hazelton (Denver, Pa.). Tissue culture plates, antibiotics, protease inhibitors and deoxycholate were from Sigma (St. Louis, Mo.). Thin layer chromatography plates were from Analtech (Newark, Del.). Authentic phospholipid standards were from Avanti Lipids (Birmingham, Al.). Protein determinations were performed according to the method of Bradford according to Bio-rad instructions (Richmond, Calif.). Peroxidase-conjugated goat anti-rabbit IgG antibodies were from Cappel (Malvern, Pa.). Anti-actin antibodies were from Amersham (Arlington Height, Ill.). Scintillation fluid and silica based affinity supports were from Beckman Instruments (Fullerton, Calif.). Synthetic melittin was from Penninsula Laboratories (Belmont, Calif.). Iodo-beads were from Pierce (Rockford, Ill.).

Patients

All patients with rheumatoid arthritis presented definite or classical symptoms as defined by the American Rheumatism Association (Ropes (1968) Bull. Rheum. Dis. 9: 175–176). Disease severity was assessed by the standard roentgenographic and clinical criteria of Steinbrocker et al. (1949) JAMA 140: 659–662. Progression of rheumatoid arthritis was defined as stage 1 or early on the basis of no destructive changes on roentgenographic examination. Stage 2 or moderate disease was defined as roentgenographic evidence of osteoporosis without joint deformities. Stage 3 or severe disease was defined on the basis of roentgenographic evidence of cartilage and bone destruction with joint deformity. Stage 4 or terminal disease was defined on the basis of fibrous or bony ankylosis. Functional capacity was defined as class 1 with complete functional capacity, class 2 as functional capacity adequate to perform normal activities despite discomfort or limited mobility and class 3 as able to perform few or no activities associated with occupational or normal life routines. Class 4 was defined as complete immobilization with the patient bedridden or wheelchair bound. Control patients with osteoarthritis (non-inflammatory arthritis) and other arthropathies also met American Rheumatism Association criteria (Huth (1986) Ann. Intern. Med. 102: 553. Normal volunteers were also used and were free of prescription medication or other drugs.

Table 2 shows clinical characteristics of rheumatoid arthritis patients.

TABLE 2

CLINICAL CHARACTERISTICS OF RHEUMATOID ARTHRITIS PATIENTS*

| | Mean (+SD) |
|---|---|
| Age (years) | 53.5 ± 14.1 |
| Sex | 28 Male, 28 Female |
| Disease Duration (months) | 110.6 ± 113.7 |
| Synovial Fluid WDC (cells/mm3) | 24,620 ± 6633 |
| NSAID | 53 Yes |
| DMARD | 37 Yes |
| Prednisone | 18 Yes |
| Westergren Sedimentation Rate | 54.5 ± 39 |
| Rheumatoid Factor (titer) | 1:1405 |
| Number of A.C.R. Criteria | 8.1 ± 1.1 |
| Stage of Progression | 2.2 ± 0.8 |
| Functional Class | 2.5 ± 0.6 |

*Snyovial fluid samples from 56 patients were examined. The abbreviations are NSAID (non-steriodal anti-inflammatory drug), DMARD (disease modifying anti-rheumatic drug), and ACR (American College of Rheumatology). All patients on prednisone were on 10 mg/day or less. Fourteen patients were rheumatoid factor negative. The median rheumatiod factor titer in patients in whom it was present was 1:640, although the mean of all positive patients were 1:1405. The A.C.R. Criteria and Stage of Progression and Functional Class are as noted above.

Synovial Fluid

Synovial fluid was obtained from Arthritis Center Clinical Laboratories (Veterans Administration Medical Center, Philadelphia, Pa. and Rheumatology Division, Bowman Grey School of Medicine, Winston-Salem N.C.) after white cell count, gram stain, and examination using polarized light microscopy. Fluids were centrifuged to remove any cells and stored at −70° C.

Definition of PLAP Activity

Fractions collected during affinity or other chromatography steps were assayed as described in Clark M. A. et al. (1987) J. Biol. Chem. 262: 4402–4406, the disclosures of which are hereby incorporated by reference as if fully set forth herein. Twenty microliter aliquots of each fraction were assayed in triplicate for endogenous phospholipase $A_2$ ($PLA_2$) and phospholipase C (PLC) activity in human U937 cell free sonicates and for the ability to stimulate $PLA_2$ activity above controls. PLAP stimulatory activity was defined as the difference between the activity observed with cell free sonicates and endogenous activity observed for each individual fraction. One unit of stimulatory activity was defined as the amount of PLAP required to produce a 2-fold increase in measured $PLA_2$ activity per 1 mg of U937 cell free sonicate protein. PLAP purified from synovial fluid was stable for several weeks at −70° C. and could be frozen and thawed 3 times without loss of activity.

Phospholipase Assays

Phospholipase $A_2$ ($PLA_2$) and phospholipase C (PLC) activities were quantified radiometrically as described in Clark M. A. et al. (1981) J. Biol. Chem. 262: 10713–10718; Bomalaski et al. (1985) J. Leukocyte Biol. 38: 649–654; and clark et al. (1986) J. Biol. chem. 261: 10713–10718, the disclosures of all of which are hereby incorporated by reference as if fully set forth herein, except that reactions were buffered with 200 mM Tris pH 9.0. For $PLA_2$ and PLC formation of lysophospholipid and diglyceride generation was measured respectively.

ELISA Assay

Twenty microliters per well of synovial fluid was deposited in wells of a microtiter plate with each well then being filled to capacity with phosphate buffered saline (PBS) containing 20% fetal calf serum. The plates were then incubated at 4° C. overnight. Rabbit anti-melittin or anti-PLAP (recombinant or purified protein or fragments thereof) antibodies were diluted 1–1000 in PBS and 50 μl added per well. For control experiments anti-actin antibodies diluted 1–1000 were substituted for the anti-mellittin or anti-PLAP antibodies. Neither anti-actin nor pre-immune antisera showed immunopositive reactions with synovial fluid from normal volunteers or arthritic patients. After overnight incubation with antibodies, plates were further incubated at room temperature for 1 hour and then rinsed 3 times (5 minutes each) with PBS. 50 μl of peroxidase conjugated goat anti-rabbit antibody (diluted 1–5000 in PBS) was then added to each well followed by a 1 hour incubation at room temperature and 3 washes (5 minutes each). O-phenylenediamine (a peroxidase substrate) was added (100 μl of a 1 mg/ml in 0.1M citrate buffer, pH 4.5, 0.12% $H_2O_2$ solution and allowed to react for 10 minutes. The reaction was stopped by the addition of 25 μl of NaF (0.1M) to each well. Absorbance for each well was determined using a Titertek Multiscan model MC (Helsinki, Finland) ELISA plate reader at 490 nm. Anti-melittin or PLAP antibodies did not cross react with other molecules, including complement cascade components.

In order to quantitate the presence of PLAP as a function of the presence and stage of rheumatiod arthritic disease ELISA assays were performed on a broad spectrum of synovial fluid samples drawn from rheumatoid arthritic patients, normal healthy volunteers, and patients with other form of arthritis or joint disease. This data is summarized in Table 3. As shown specimens from patients with rheumatoid arthritis showed an average 4.3-fold increase in PLAP levels over healthy synovial fluid or fluid from patients with osteoarthritis. Within the detection limits of the assay 87% of rheumatoid arthritic patient synovial fluid showed elevated PLAP levels. Elevated levels of PLAP were detected in rheumatoid arthritic patients and increased levels of the activating protein were associated with severity of the disease ($p<0.05$).

TABLE 3

ELISA Assay for PLAP*

| Arthritis Value | Number | ELISA Value | p |
|---|---|---|---|
| Rheumatoid | 32 | 1.88 ± 1.19 | — |
| Osteoarthritis | 12 | 0.44 ± 0.62 | 0.05 |
| Pseudogout | 5 | 0.20 ± 0.44 | 0.05 |
| Seronegative Spondyloarthropathy | 5 | 0.28 ± 0.68 | 0.05 |

*Expressed as optical density (o.d.)

For experiments using BC3H1 smooth muscle cells, cells were grown in 96 well plates to 75% confluence over 2–3 days and treated in quadruplicate with leukotriene D4 (1 μM) for varying time periods. Reactions were stopped by the addition of formalin to a final concentration of 3% V/V. Cells were permeabilized with 0.05% Tween 20 and reacted with anti-melittin antibodies (diluted 1–100) for 1 hour. Quantification of bound antibody was performed using a peroxidase conjugated second antibody (Malloy Labs) according to manufacturers' instructions.

Localization of PLAP in Synovial and Rheumatoid Nodule Tissue

Synovial tissue from 6 patients with definite or classical rheumatoid arthritis and 6 patients with osteoarthritis who had undergone total joint replacement and subcutaneous nodules from 2 rheumatoid patients with classical disease were processed by routine histologic methods for pathological examination. Bone specimens were prepared calcified and decalcified. Immunochemical localization of PLAP was performed using anti-melittin or anti-PLAP antibodies.

Isolation of PLAP from Human Synovial Fluid

PLAP isolation from human synovial fluid was performed essentially as described in Clark M. A. et al. (1987) J. Biol. Chem. 262: 4402–4406, the disclosures of which are hereby incorporated by reference as if fully set forth herein. Affinity purified anti-melittin antibodies in PBS were immobilized on activated affinity silica supports and the columns equilibrated with PBS containing the protease inhibitors phenymethylsulfonyl fluoride (10 μM), bacitracin (100 μg/ml), benzamidine (1 mM), soybean trypsin inhibitor (5 g/ml) and Tween 20 (0.05%). Prior to chromatography synovial fluid was centrifuged at 13,000×g for 10 minutes. The resulting supernatant was diluted 1:1 with PBS and applied to the silica column at a flow rate of 0.1 ml/minute at room temperature. The column was washed for 5 minutes (2 ml/minute) with PBS and eluted with 50 mM sodium acetate pH 3.1 (0.5 ml/minute). Fractions containing PLAP activity were pooled and further purified by HPLC size exclusion chromatography using a TSK3000 sw HPLC column equilibrated with PBS containing 0.05% Tween 20 at a flow rate of 0.5 ml/min. SDS polyacrylamide gel electrophoresis using 15% T gels was performed to assess protein purity. Samples for electrophoresis were iodinated using $^{125}I$ and Iodobeads (Pierce) according to the manufacturers' instructions.

No lipopolysaccharide contaminants were observed in purified PLAP fractions used for in vivo testing as measured by the limulus amibocyte assay (detection limit 0.1 5 ng/ml).

Figure 4:
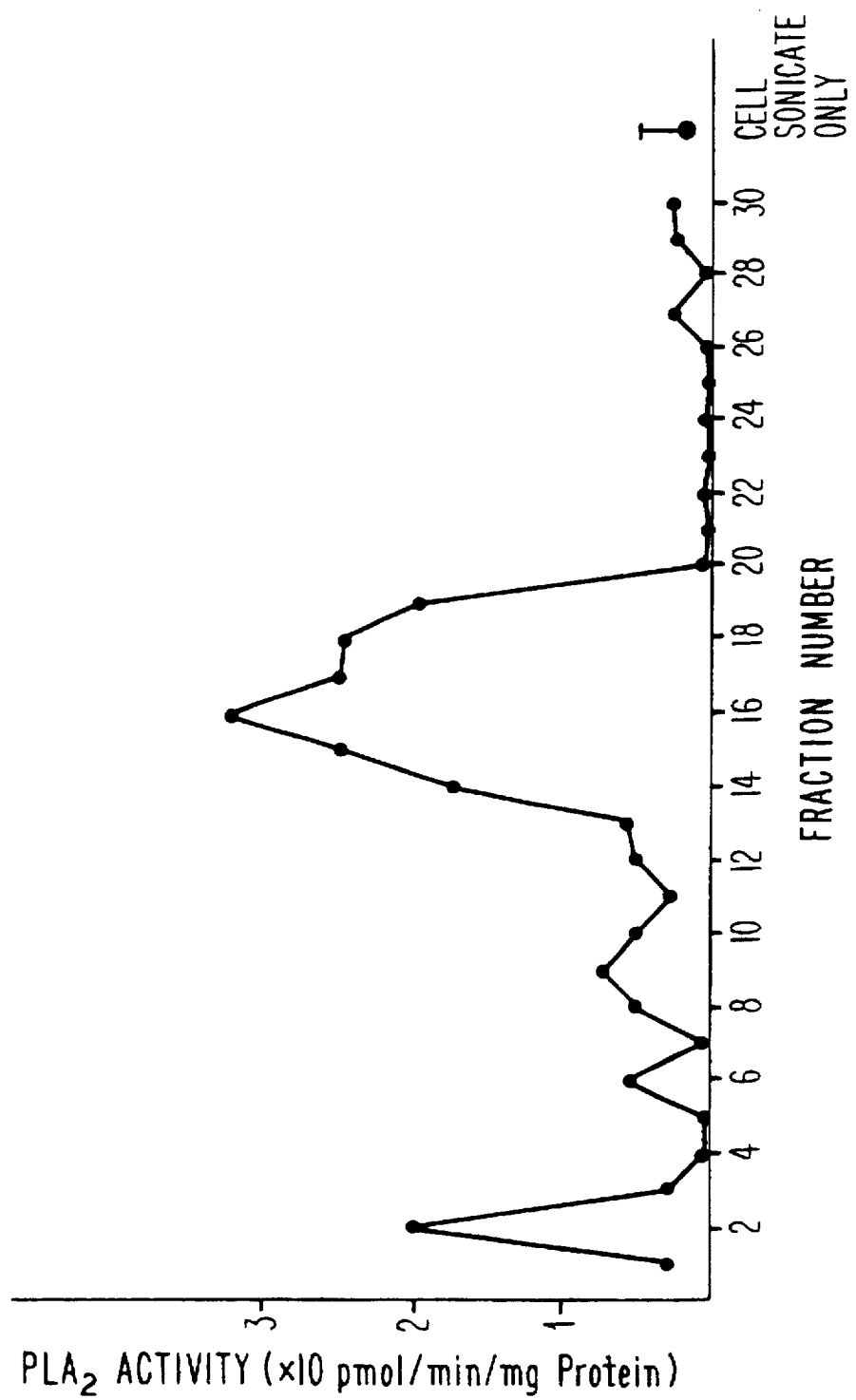
FIG. 4 shows a graph of the PLA$_2$ activity of fractions of PLAP collected from a size exclusion chromatography column during purification of PLAP from human synovial fluid.

Purification of PLAP from human synovial fluid by affinity chromatography using silica immobilized anti-melittin antibodies is illustrated in FIG. 3. Purification of PLAP to homogeneity by size exclusion HPLC using a silica based size exclusion column is illustrated in FIG. 4. Fractions were assayed for PLAP activity as described herein. An aliquots of pooled and concentrated fractions were iodinated using $^{125}I$ and subjected to SDS polyacrylamide gel electrophoresis. A single band at 28000 molecular mass was observed on autoradiography of the electrophoresis gel. The estimated molecular size of the protein from the size exclusion column (43000 molecular mass) may reflect an artifact due to the presence of detergents or an oligomeric structure for PLAP. Similar results were obtained using anti-rPLAP antibodies although silica is the preferred support for immobilization due to lower sample dilution.

Phospholipase Specificity of PLAP Isolated from Human Synovial Fluid

The phospholipase specificity of PLAP was examined using the major phospholipids listed in Table 4. Rheumatoid synovial fluid PLAP was found to be specific for phosphatidylcholine preferring $PLA_2$ and did not affect phospatidylethanolamine or phosphatidylinositol activities. PLC activity was not affected by PLAP. These results are qualitatively similar to PLAP isolated from other mammalian sources (Clark et. al. (1987) J. Biol. Chem. 262: 4402–4406 and Clark et al. (1988) Biochem. J. 250: 125–132. rPLAP isolated as a fusion protein was devoid of phospholipase stimulatory activity.

TABLE 4

Phospholipid Substrate Specificity of PLAP*

| | Sonicate alone | PLAP alone | Sonicate plus PLAP (1 unit) |
|---|---|---|---|
| Phospholipase $A_2$ | | | |
| Phosphatidylcholine | 7.9 ± 0.2 | BG | 16.1 ± 1.9** |
| Phosphatidylethanolomine | 2.5 ± 0.5 | BG | 2.0 ± 0.3 |
| Phosphatidylinositol | <0.1 | BG | <0.1 |
| Phospholipase C | | | |
| Phosphatidylcholine | 1.9 ± 0.3 | BG | 2.1 ± 0.2 |
| Phosphatidylinositol | 0.6 ± 0.2 | BG | 0.6 ± 0.1 |

*Expressed as pmol of product produce/mg cell protein using U937 monocytes as a source of $PLA_2$. One unit of PLAP was defined as that amount of PLAP required to produce a 2-fold increase in the observed phospholipase $A_2$ activity found per mg protein of U937 cells, and was diluted to a final volume of one unit of PLAP per 10 ul of buffer. BG = background. Boiled PLAP had no phospholipase $A_2$ stimulatory activity.
**$p < 0.05$ compared to sonicate alone by Student's t-test.

Cell Culture

Human monocyte U937 cells were a gift from Dr. Giorgio Trinchieri of the Wistar Institute (Philadelphia, Pa.) or were purchased from the American Type Tissue Culture Collection (Bethesda, Md.) accession number CRL 1593, and were maintained in RPMl 1640 supplemented with 10% heat inactivated fetal calf serum. Cells were used during the log growth phase. BC3H1 murine smooth muscle cells and CPAE bovine endothelial cell lines were also obtained from the American Type Tissue Culture Collection accession numbers CRL 1443 and CRL 209, respectively. Cells were grown in Dulbecco's Modified Minimal Essential Media containing 20% fetal calf serum in 95% air, 5% $CO_2$.

Injection of PLAP and PLAP Derived Synthetic Peptides into Rabbit Joints

Male New Zealand white rabbits weighing 3–4 kg (3 per group) were anesthetized and prepared for surgery according to standard protocols. Rabbits were injected in the knee joint with 1 ml of sterile pyrogen free purified synovial fluid PLAP (containing 3000–100000 units in saline) and in the contralateral knee with an equal volume of pyrogen free saline or saline containing 0.15 ng/ml lipopolysaccharide or 10 μg/ml actin. Additional controls were pooled size exclusion HPLC fractions devoid of PLAP activity concentrated and processed as for PLAP or boiled denatured PLAP preparations. Injections were made through the lateral joint capsule so as to avoid the infrapatellar fat pad. Twenty four hours post-injection the rabbits were necropsied and both knees ravaged with 2 ml of pyrogen free saline prior to opening. The lavage fluid was cultured for bacteria and the total and differential cell count determined. An aliquot of the lavage fluid was centrifuged and the supernatant frozen and stored at −70° C. until radio-immunoassay, using radioimmune assay kits (New England Nuclear, Boston, Mass.) according to instructions, for prostaglandin $E_2$ and leukotriene $C_4$. The synovial lined infrapatellar fat pad portion from each joint was also excised and fixed in formalin and embedded in paraffin for routine histology. Bacterial cultures of synovial fluids were negative.

PLAP stimulation of an inflammatory arthritogenic response was examined by injection of purified PLAP into rabbit knee joints. Saline, boiled (denatured) PLAP as well as the protein controls described above were injected into the contra lateral joint. The dose-response relationship of PLAP in mediating an inflammatory arthropathy with cellular infiltration and joint destruction is summarized in Table 5. After 24 hours post-injection of (3000–50000 PLAP units)

the total cell count of synovial lavage fluids was dramatically increased. Although the majority of inflammatory cells present were polymorphonuclear leukocytes (95% PMN), there was an absolute increase in mononuclear inflammatory cells as well. After 24 hours post-injection with 3000 PLAP units fewer PMN and more monocytes were observed.

Histologically, with up to 50000 PLAP units there was a dose related inflammatory cell infiltration of the infrapatellar fat pad primarily located immediately beneath and within the synovial lining. Synovial proliferation was also observed. After injection of 100000 PLAP units, the inflammatory cell infiltrate was markedly reduced. This reduction was associated with hemorrage, necrosis and loss of synovial lining cells and further accompanied by multifocal-necrosis and hemorrage of the tunica media arterioles. These data demonstrate the ability of PLAP to mediate synovial fluid leukocytosis and inflammatory synovitis with mild inflammation to gross tissue damage depending on dose.

When PGE2 levels were measured in lavage fluid post-injection of 50000 PLAP units a slight increase was observed over controls (0.1 ng/ml). No LTC4 was detected. In control experiments, no tissue damage or inflammatory cell infiltration was observed.

TABLE 5

Induction of Synovial Fluid Leukocytosis in Rabbits*

| Compound Injected | WBC (×10⁵)/ml |
| --- | --- |
| Actin (10 µg/ml) | 1.1 ± 0.2 |
| LPS (0.15 ng/ml) | 9.1 ± 0.1 |
| HPLC Eluent | 12.3 ± 2.1 |
| Boiled PLAP (60,000 units/ml) | 10.8 ± 0.8 |
| PLAP (3,000 units/ml) | 38.6 ± 15.4** |
| PLAP (6,000 units/ml) | 51.2 ± 8.1** |
| PLAP (25,000 units/ml) | 68.3 ± 16.4** |
| PLAP (50,000 units/ml) | 73.5 ± 13.5** |
| PLAP (100,000 units/ml) | 6.2 ± 2.9 |

*PLAP isolated from the HPLC gel filtration column was injected into rabbit knee joints. Control joints were injected with actin, LPS or HPLC gel filtration eluent. The amount of LPS injected was the amount detectable by this assay. Eluent from HPLC fractions without PLAP activity was concentrated 16-fold prior to injection. After twenty four hours, the rabbits were necropsied and the knee synovial cavity was lavaged with 2 ml of phosphate buffered saline.
**p < 0.05 by Student's t-test compared to HPLC eluent or boiled PLAP.

Uptake and Release of (3H) Arachidonic Acid

Normal human peripheral blood monocytes in 24 well tissue culture plates were incubated with labelled arachidonic acid for 24 hours as described in Bomalaski J. (1986) Clin. Immunol. Immuopath. 39: 198–212, the disclosures of which are hereby incorporated by reference as if fully set forth herein. The mononuclear leukocytes were then separated using Ficoll-Hypaque according to conventional methods, washed, resuspended in RPMI-1640 media containing 10% heat inactivated fetal calf serum (complete media) and allowed to adhere for 1 hour. Nonadherent cells were removed by a wash with PBS and overlayed with labelled arachidonic acid for 24 hours. Cells were washed twice with PBS and reincubated with complete media or complete media containing 10 units/ml PLAP. At appropriate time points aliquots of cell supernatant were taken and counted by scintillation spectrometry. Cell viability was determined by trypan blue dye exclusion. Lactate dehydrogenase release assays showed identical results for control and treated cells.

Induction of Eicosanoid Generation in Peripheral Blood Cells

Human peripheral blood monocytes and reticulocytes were prepared by standard methods. Cells were incubated with PLAP for various times, centrifuged and the supernatants recovered for assay. Using radioimmunoassay kits (New England Nuclear, Boston, Mass.) leukotriene $B_4$ and prostaglandin $E_2$ release were measured.

Figure 5:
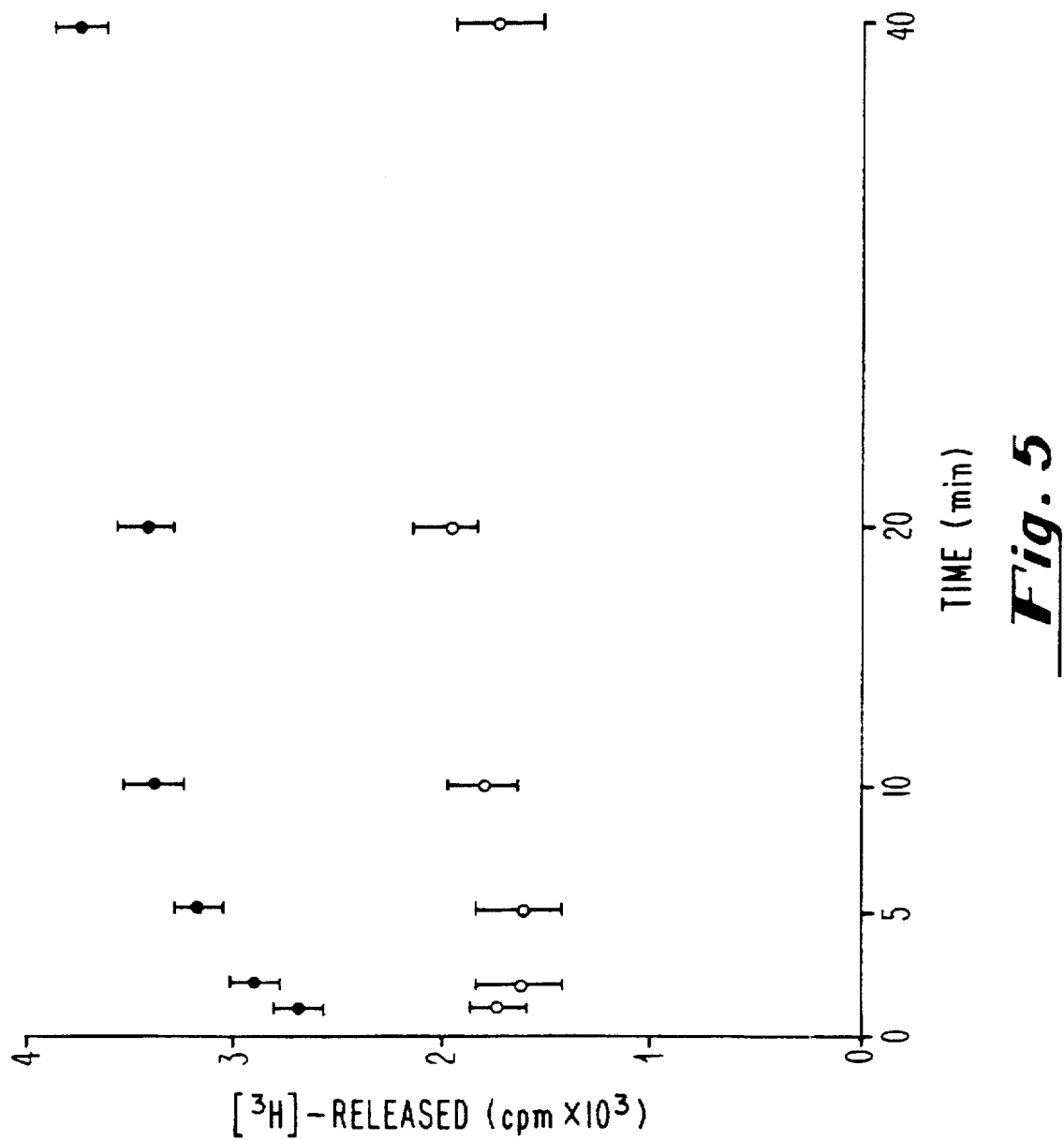
FIG. 5 shows PLAP induced release of [$^3$H]-arachidonic acid metabolites from human peripheral blood monocytes.

To demonstrate PLAP induction of eicosinoid release, normal human peripheral blood monocytes preloaded with labelled arachidonic acid were stimulated with PLAP. A signifigant release of arachidonic acid metabolites was observed as summarized in FIG. 5. Radioimmunoassay for specific metabolites of unlabelled cells showed prostaglandin $E_2$ as the major metabolite released as shown in Table 6. Similarly PLAP was shown to stimulate release of leukotriene $B_4$ and prostaglandin $E_2$ (Table 6).

TABLE 4

PLAP and PHOSPHOLIPASE $A_2$ STIMULATE EICOSANOID RELEASE*

| | Human Monocyte Prostaglandin $E_2$ (pg/2.5 × 10⁶ cells) Time (min) | | Human Neutrophil Leukotriene $B_4$ (pg/2 5 × 10⁶ cells) Time (min) | |
| --- | --- | --- | --- | --- |
| Treatment | 5 | 20 | 5 | 20 |
| Buffer | 0 | 2 | 5 | 21 |
| PLAP (1 unit) | 2 | 7 | 13 | 28 |
| Metlittin (10 ug) | 28 | 71 | 28 | 41 |
| $PLA_2$ - Porcine (14 pmol) | 0 | 7 | 167 | >300 |
| $PLA_2$ - Bovine (14 pmol) | 7 | 30 | 234 | >300 |

*Human peripheral blood monocytes and neutrophils were prepared as described. Cells were placed in 1 ml microfuge tubes and incubated at 37° C. for five or twenty minutes with the indicated compounds. The tubes were then centrifuged, and the supernatants taken for by radioimmunoassay. Each sample was prepared in duplicate, and is expressed as the mean value; standard deviation was within 1.0%. Data from a representative experiment of which three were performed.

Localization of PLAP in Rheumatoid Synovial and Subcutaneous Nodule Tissue

To determine the cellular source of PLAP found in human joints, metacarpophalangeal and knee joint specimens were obtained from patients with rheumatoid arthritis or osteoarthritis and immunohistochemical staining with anti-PLAP antibodies performed. All 6 rheumatoid arthritic patients tested displayed intense staining. No staining was observed with the specimens obtained from osteoarthritic patients.

Microscopic examination revealed heavy staining of synovial monocytes, macrophages, and multinucleated giant cells with some additional staining of vascular smooth muscle and endothelial cells. Similar results were observed in rheumatoid nodules. Osteoarthritic synovium revealed no PLAP staining even under microscopic examination. No staining was observed in either specimen type with pre-immune antisera.

Statistical Data Analysis

Data was analyzed using the students t-test or where appropriate the Spearman linear rank correlation coefficient or Wilcoxon correlation using as SSPS Inc. Data Programming Model (Chicago, Ill.). The number of samples required to avoid a Type 2 error was determined as described in Young (1983) Annal. Intern. Med. 99: 248–251. For the animal data a randomized complete block analysis of variance LSD test was used to compare differences between the treatment means. An alpha of 0.05 was used as a criteria for signifigance (SAS Manual).

Molecular Cloning of PLAP

Unless otherwise stated, purification and cloning was performed according to standard techniques such as those found in Sambrook, et al., *Molecular Cloning, A Laboratory Manual*, second edition, Cold Spring Harbor Laboratory Press; Cold Spring Harbor, N.Y. (1989).

BC3H1 cells were treated with leukotriene LDT$_4$ (1 μM) for 2 minutes prior to extraction of total cellular RNA with guanidine isothiocyanate to increase synthesis of mRNA coding for PLAP. PolyA containing RNA was selected by affinity chromatography on oligo(dT) cellulose.

A cDNA library was then prepared utilizing the polyA selected RNA. The first strand of cDNA was synthesized by reverse transcriptase using an oligo dT primer. The second strand of cDNA was synthesized using DNA polymerase I and E. coli DNA ligase according to the method of Gubler and Hoffman (1983) Gene 25: 263–279. EcoR1 linkers (Vector Labs, Burlingame, Calif.) were added and the inserts ligated to λgt11 (Vector Labs, Burlingame, Calif.) according to the manufacturers' protocol. The resulting library was screened to identify clones containing DNA coding for PLAP according to the method of Young and Davis (1983) Proc. Natl. Acad. Sci. USA 80: 1194–1199, and Snyder, M. et al. Method Enzymol. 154: 107–128 (1984). Anti-melittin antibodies were prepared according to the method of Clark et al. (1988) Biochem. J. 250: 125–132, and Clark et al. (1987) J. Biol. Chem. 262: 4402–4406, the disclosures of both of which are hereby incorporated by reference as if fully set forth herein.

The positive cDNA clone identified by screening with anti-mellitin antibodies was subcloned into M13 and sequenced using the dideoxy method described in Sanger et al., (1980) J. Mol. Biol. 143: 161–169, and Snyder, M. et al., supra. Enzymes and other necessary reagents were obtained from US Biochemical Corporation, Cleveland, Ohio. The sequence of this clone is shown in FIG. 2 (SEQ ID NO: 1).

Expression of rPLAP in BC3H1 Cells

The metallothionein promoter described by Brinster et al. Nature 296: 39–42 was chemically synthesized and ligated into the plasmid pUC19 (Southern and Berg (1982) J. Mol. Appl. 1: 327–341) containing a neomycin resistance gene. The cDNA coding for PLAP was excised from the lambda gt 11 clone using EcoR1 and ligated into pUC19 downstream from the metallothionein promoter.

The PLAP pUC19 expression vector was transfected into BC3H1 cells by electroporation using 100 μg of DNA/10$^6$ cells and a BioRad electroporation device using the setting of 250 volts and 25 μFd. Cells were grown in Dulbecco's Modified Minimal Essential Medium (GIBCO, Grand Island, N.Y.). Stable transformed cells were then selected by growth in medium supplemented with neomycin (0.3 mM) (G418, GIBCO, Grand Island, N.Y.). Transformed cells were incubated overnight in [$^3$H]-arachidonic acid (10 μCi/ml). The next day the cells were rinsed three times in saline before being treated with copper. Aliquots of the supernatant (1 ml) were collected at predetermined times and the amount of radioactivity released was determined by liquid scintillation spectroscopy. Clones containing the PLAP cDNA insert in the 5' to 3' orientation increased the rate of release of radioactive arachidonic acid metabolite following treatment with copper, whereas cells which contained the PLAP cDNA clone in the 3' to 5' orientation appeared to suppress the release of [$^3$H]-arachidonic acid and its metabolites.

Antibody Production Using Recombinant PLAP (rPLAP)

Antibodies were generated to recombinant PLAP (rPLAP) prepared as a β-gal-PLAP fusion protein. The β-gal fusion protein was prepared according to the method disclosed in Snyder, M. et al. (1984) Methods in Enzymology 154: 107–128, the disclosures of which are hereby incorporated by reference as if fully set forth herein. Briefly, E. coli 1089 cells were infected with the lambda clone containing the PLAP cDNA and producing lysogens. Next the cells were grown at 30° C. to a OD$_{600}$ of 0.4 and the synthesis of the β-gal PLAP fusion protein induced by a shift to 37° C. in the presence of isopropyl-B-D-thiogalactoside (IPTG, 100 μg/ml) for 1 hour. The cells were then harvested, placed in SDS sample buffer [Laemmli, U.K. (1970) Nature 227: 680–685] and frozen. The fusion protein isolated by preparative SDS polyacrylamide electrophoresis using a 6% polyacrylamide gel. The band containing the fusion protein was identified by its increased synthesis in response to IPTG treatment and by Western blot analysis using anti-melittin antibodies. The band, which was well-resolved from other proteins, was excised and crushed, mixed with adjuvant and injected subcutaneously into female New Zealand White rabbits (100 μg/injection) according to standard protocols. Control antisera to β-galactosidase was purchased from Bethesda Research Laboratories, Bethesda, Md.

Affinity Purification of PLAP Using Anti-rPLAP Antibodies

Immunoglobulin enriched fractions of the antisera were prepared by ammonium sulfate precipitation. The resulting IgG enriched fraction was next immobilized on cyanogen bromide activated Sepharose (Pharmacia, Uppsala, Sweden) as suggested by the manufacturer. PLAP was immuno purified as described in Clark, M. A. et al. (1988) Biochem. J. 250: 125–132, and Clark, M. A. (1987) J. Biol. Chem. 262: 4402–4406, the disclosures of both of which are hereby incorporated by reference as if fully set forth herein, except that anti rPLAP antibodies were substituted for anti-melittin antibodies. Briefly, whole cell sonicates made from CPAE cells were passed over the column which was washed extensively before eluting the bound material with low pH buffer (50 mM sodium acetate pH 3.1). The resulting fractions were assayed for their ability to stimulate PLA$_2$ activity as described herein.

Synthesis of Single Stranded Antisense DNA and PLAP Peptides

Single stranded DNA was prepared chemically using a Beckman or Pharmacia DNA synthesizer according to instructions for phosphoramidite based reagents. Synthetic PLAP peptides were prepared using a Milligen/Biosearch (Milford, Mass.) peptide synthesizer according to instructions for t-BOC amino acids. Purified peptides were prepared by standard HPLC methods.

Northern Blot Analysis of PLAP mRNA Induction

CPAE or BC3H1 cells were treated with leukotriene D4 (1 μM) for varying time periods and total RNA extracted using hot phenol (65° C.). Extracted RNA was electrophoresed on a gel prepared from 1% agarose (10 μg/lane) and blotted onto nitrocellulose membrane according to standard procedures. Probing was performed using a PLAP cDNA clone which had been nick labelled with $^{32}$P dCTP.

Assay for PLAP Neutralizing Activity

PLAP (10 units) purified as described herein was incubated with 2 μl of ammonium sulfate purified anti-rPLAP antibody. The antibody PLAP solution was added to whole cell sonicates and PLA$_2$ activity assayed as described herein. Anti-melittin antibodies were found to have no neutralizing activity against PLAP.

Antisense, PLAP, and the Treatment of Rheumatoid Arthritis

Antisense experiments were performed in order to assess the role of PLAP protein synthesis in the activation of PLA$_2$ in endothelic cell sin response to inflammatory stimuli. It has recently been shown that direct addition of synthetic antisense DNA to cultured cells specifically disrupts the synthesis of protein [Graham F. L., Vandereb A. J. (1973) Virology 52:456–463; Heikkila R., Schwap G., Wickson, E. Pluzink D. H., Watt R., Neekers L. (1987) Nature 328:445–449]. A single strand of antisense DNA homologous to the first 20 bases of the 5' end of the open reading frame of the PLAP cDNA clone was synthesized. The antisense sequence had the following sequence: CAC-TATATGAGCGGCCACTCTAATT (SEQ ID NO: 17) (which is the sequence between the arrows in FIG. 2). This DNA was then added to CPAE bovine endothelial cells at a concentration of 25 mM for approximately 4 hours prior to the start of the experiment. The addition of antisense to the cell successfully abolished the induction of PLAP protein synthesis following LTD4 treatment (1 μM) as determined by ELISA assay. $PLA_2$ activity, arachidonic acid release and prostacyclin synthesis were also inhibited. These results are summarized in Tables 7, 8 and 9. In Table 8, antisense or irrelevant DNA was added to the cells is prior to the measurement of phospholipase $A_2$ activity as described herein. All values are expressed as pmol of reaction product produced per min per mg of protein. In Table 8, cells were incubated with $^3H$-arachidonic acid 10 μCi/ml overnight next antisense or irrelevant DNA was added to the culture 25 μM for four hours prior to the addition of LTD. The amount of radiolabeled secreted into the supernatant following ten minutes of treatment was quantitated. All values are expressed as cpm released by $10^5$ cells following ten minutes of treatment. In Table 9, cells were incubated with antisense DNA or irrelevant DNA 25 μM for four hours prior to the addition of $LTD_4$ (1 μM). The amount of prostacyclin released by the cells were quantitated by radioimmunoassays.

From these experiments it was concluded that the mechanism by which LTD4 increases prostacylin production in these bovine endothelial cells requires that the cells first synthesize PLAP mRNA, an event inhibitable by actinomycin D treatment. Next the PLAP mRNA must be translated in order for mature PLAP protein to be made. Translation of the PLAP message can be inhibited using cycloheximide or antisense PLAP DNA. Irrespective of the method of inhibition it is clear that production of PLAP is a key step in the release of arachidonic acid following leukotriene stimulation and that the cellular response to the increased biosynthesis following leukotriene stimulation is determined by the ability of the cells to selectively express PLAP.

TABLE 7

EFFECTS OF ANTISENSE DNA ON $LTD_4$ ACTIVATION OF $PLA_2$

| Treatment | Control | +$LTD_4$ |
|---|---|---|
| None | 7.0 ± 0.5 | 22.0 ± 2.0 |
| Antisense DNA | 6.0 ± 1.0 | 9.1 ± 1.1 |
| Control DNA | 6.0 ± 1.4 | 19.0 ± 2.0 |

TABLE 8

EFFECTS OF ANTISENSE DNA ON $LTD_4$ INDUCED RELEASE OF ARACHIDONIC ACID

| Treatment | Control | +$LTD_4$ |
|---|---|---|
| None | 4680 | 11680 |
| Antisense DNA | 4755 | 5516 |
| Control DNA | 4910 | 11180 |

TABLE 9

EFFECTS OF ANTISENSE DNA ON $LTD_4$ INDUCED $PGI_2$ SYNTHESIS

| Treatment | Control | +$LTD_4$ |
|---|---|---|
| None | 2.4 ± 0.6 | 4.3 ± 0.4 |
| Antisense DNA | 2.2 ± 0.5 | 2.1 ± 0.4 |
| Control DNA | 2.1 ± 0.6 | 4.4 ± 0.5 |

We claim:

1. A method for detecting elevated levels of phospholipase A2 activating protein in a person expected of having rheumatoid arthritis to thereby indicate the presence of rheumatoid arthritis in said person comprising the steps of:
   providing a sample of serum from said person;
   contacting said sample with an antibody specific for phospholipase A2 activating protein such that said antibody binds with phospholipase A2 activating protein in said sample; and
   detecting binding of said antibody to phospholipase A2 activating protein thereby indicating the presence of phospholipase A2 activating protein, whereby elevated levels of phospholipase A2 activating protein in said sample as compared with levels found in persons not having rheumatoid arthritis indicates the presence of rheumatoid arthritis in said person.

* * * * *

UNITED STATES PATENT AND TRADEMARK OFFICE
CERTIFICATE OF CORRECTION

PATENT NO. : 5,786,154
DATED : July 28, 1998
INVENTOR(S) : Bomalaski et al.

It is certified that error appears in the above-indentified patent and that said Letters Patent is hereby corrected as shown below:

In column 7, line 9 (in Table I corresponding to Peptide F) under SEQ ID NO: delete "-" and insert - 13 - therefor.

In column 8, line 18 delete "leaving" and insert - having - therefor.

In column 14, line 49 delete "ravaged" and insert - lavaged - therefor.

In column 16, line 31 after "taken for" insert - eicosanoid determination -.

In column 19, line 12 delete "Table 8" and insert - Table 7 - therefor.

Signed and Sealed this

Fifth Day of January, 1999

Attest:

Attesting Officer

*Acting Commissioner of Patents and Trademarks*

UNITED STATES PATENT AND TRADEMARK OFFICE
CERTIFICATE OF CORRECTION

PATENT NO. : 5,786,154
DATED : July 28, 1998
INVENTOR(S) : Bomalaski et al.

It is certified that error appears in the above-identified patent and that said Letters Patent is hereby corrected as shown below:

Column 2,
Line 47, delete "FIG. 2 shows" and insert -- Figures 2A, 2B, 2C, and 2D --

Column 3,
Line 24, delete FIG. 2"and insert -- Figures 2A, 2B, 2C, and 2D --.

Signed and Sealed this

Twentieth Day of November, 2001

*Attest:*

*Attesting Officer*

NICHOLAS P. GODICI
*Acting Director of the United States Patent and Trademark Office*

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 2553 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 256..1230

( i x ) FEATURE:
        ( A ) NAME/KEY: mat_peptide
        ( B ) LOCATION: 256..1230

( x i ) SEQUENCE DESCRIPTION: SEQ ID NO:1:

```
AACGACGGCC  AGTGAAATTC  CGCCGGCTCG  GGCCTGTGGA  CGAGTCTCGC  GCTGTGCCCG       60

GGGCGCGCGT  CCGGATCCAC  GCTGGCCATG  GCGAGCGCGC  CTCCAGATAC  CGGCTGAGCT     120

GCTCGCTACC  GGGCCACGAA  CTGGACGTGA  GGGCCTGGT   GTGCTGCCTC  TACCCGCCGG     180
```

```
AGCCTTTGTG TCTGTGTCCC GGGATCGACC ACCCGCCTCT GGGCTCCAGA CAGTCCTAAC        240

AGGGGCTTTA CAGAA ATG CAC TAT ATG AGC GGC CAC TCT AAT TTT GTG TCT        291
            Met His Tyr Met Ser Gly His Ser Asn Phe Val Ser
            1             5                       10

TAT GTG TGT ATC ATA CCC TCA AGT GAC ATA TAT CCT CAT GGA CTG ATT        339
Tyr Val Cys Ile Ile Pro Ser Ser Asp Ile Tyr Pro His Gly Leu Ile
        15              20              25

GCC ACT GGA GGA AAT GAC CAC AAT ATT TGC ATT TTC TCG CTG GAC AGT        387
Ala Thr Gly Gly Asn Asp His Asn Ile Cys Ile Phe Ser Leu Asp Ser
        30              35              40

CCA ATG CCA CTT TAT ATT TTA AAG GGT CAC AAA GAT ACT GTT TGT AGT        435
Pro Met Pro Leu Tyr Ile Leu Lys Gly His Lys Asp Thr Val Cys Ser
45              50              55                              60

CTT TCT TCT GGA AAA TTT GGG ACA TTA CTT AGT GGC TCA TGG GAC ACC        483
Leu Ser Ser Gly Lys Phe Gly Thr Leu Leu Ser Gly Ser Trp Asp Thr
                65              70              75

ACT GCT AAA GTC TGG CTG AAT GAC AAA TGC ATG ATG ACA TTA CAG GGT        531
Thr Ala Lys Val Trp Leu Asn Asp Lys Cys Met Met Thr Leu Gln Gly
            80              85              90

CAT ACA GCC GCA GTA TGG GCA GTA AAG ATT TTA CCT GAA CAG GGC TTA        579
His Thr Ala Ala Val Trp Ala Val Lys Ile Leu Pro Glu Gln Gly Leu
        95              100             105

ATG CTA ACT GGA TCA GCA GAC AAG ACC ATT AAA CTA TGG AAG GCT GGA        627
Met Leu Thr Gly Ser Ala Asp Lys Thr Ile Lys Leu Trp Lys Ala Gly
        110             115             120

AGA TGT GAG AGG ACT TTT TTA GGG CAT GAA GAC TGT GTA AGA GGC TTG        675
Arg Cys Glu Arg Thr Phe Leu Gly His Glu Asp Cys Val Arg Gly Leu
125             130             135             140

GCA ATC TTG AGT GAG ACA GAA TTT CTT TCC TGT GCA AAC GAT GCT AGT        723
Ala Ile Leu Ser Glu Thr Glu Phe Leu Ser Cys Ala Asn Asp Ala Ser
                145             150             155

ATT AGA AGG TGG CAG ATC ACT GGC GAG TGT CTG GAA GTA TAC TTT GGA        771
Ile Arg Arg Trp Gln Ile Thr Gly Glu Cys Leu Glu Val Tyr Phe Gly
            160             165             170

CAT ACA AAT TAT ATT TAT AGC ATA TCT GTC TTT CCA AAC TCC AAA GAT        819
His Thr Asn Tyr Ile Tyr Ser Ile Ser Val Phe Pro Asn Ser Lys Asp
        175             180             185

TTT GTG ACC ACT GCA GAA GAC AGA TCT CTA AGA ATA TGG AAA CAT GGT        867
Phe Val Thr Thr Ala Glu Asp Arg Ser Leu Arg Ile Trp Lys His Gly
        190             195             200

GAA TGC GCC CAA ACA ATC CGA CTT CCA GCT CAG TCT ATA TGG TGT TGC        915
Glu Cys Ala Gln Thr Ile Arg Leu Pro Ala Gln Ser Ile Trp Cys Cys
205             210             215             220

TGC GTA CTG GAA AAT GGT GAC ATT GTG GTT GGT GCG AGT GAT GGT ATT        963
Cys Val Leu Glu Asn Gly Asp Ile Val Val Gly Ala Ser Asp Gly Ile
                225             230             235

ATT AGG GTG TTT ACA GAG TCA GAG GAG CGG ACA GCA AGT GCT GAG GAA       1011
Ile Arg Val Phe Thr Glu Ser Glu Glu Arg Thr Ala Ser Ala Glu Glu
            240             245             250

ATC AAA GCT TCT CTC TCT CGA GAG AGT CCG TTG ATA GCT AAG GTT TTG       1059
Ile Lys Ala Ser Leu Ser Arg Glu Ser Pro Leu Ile Ala Lys Val Leu
        255             260             265

ACC ACT GAA CCC CCT ATA ATT ACG CCT GTC CGA AGG ACC CTC CCT TGT       1107
Thr Thr Glu Pro Pro Ile Ile Thr Pro Val Arg Arg Thr Leu Pro Cys
        270             275             280

AGA GTC ACT CGG TCC ATG ATC TCT TCC TGT CTG AGC AGA TTA GTC TCT       1155
Arg Val Thr Arg Ser Met Ile Ser Ser Cys Leu Ser Arg Leu Val Ser
285             290             295             300

ACC TCT CTC TCA ACT TCG GAT AGT CAC CTC ACA ATC ACT GCC CTC CAC       1203
```

| Thr | Ser | Leu | Ser | Thr | Ser | Asp | Ser | His | Leu | Thr | Ile | Thr | Ala | Leu | His |
|---|---|---|---|---|---|---|---|---|---|---|---|---|---|---|---|
| | | | | 305 | | | | 310 | | | | | 315 | | |

| CTA | TTT | TTA | ACC | ACT | ACA | ACA | ACC | GAG | TAGACCACGA | TTAGTCGTTT | | 1250 |
|---|---|---|---|---|---|---|---|---|---|---|---|---|
| Leu | Phe | Leu | Thr | Thr | Thr | Thr | Thr | Glu | | | | |
| | | | 320 | | | | | 325 | | | | |

```
GTAGACCTTT  TCAAAATATA  CTTCCCTTTC  TTAAACTAAT  ACAAAGAGT  TAGCTACACT   1310
TACTTCCACC  TGGTAGCATA  TTTAATGGTA  TATTACAGTC  ACTGCTAGGG  ACCGATCAAC   1370
GTATGTTGAA  GAACGTCTTT  TTACTAAACT  TAGGGTACAA  AGACCTAGTC  CACCGATTTA   1430
AATAATAACT  ATTGTGTTTT  CCAGTTTGTG  ACCCTGAACC  CTTATGGTCA  AAAAGTCTAG   1490
GCAAATGTCC  ACCACCAGCG  ATACAAGGTC  CTTGAAGTCC  TGGAAGGTTG  TGTCACGTCT   1550
GTCGTCTAGG  AAAGTGTCCA  CGACCCGCAA  TGTACGGTCC  AAGACGTCCA  TACCTGTGGT   1610
GGTACTGACC  TCAACTAGGT  AAATGTCCCT  TGTCACGGAT  GGCTAGTCGA  CGTAGATTTT   1670
GTCACTTGTA  AATAAAGGGG  TTTTTCTTC  GAGAATGGAA  ACTGGTTTGT  TTGGGATGTG   1730
TTTATAATCC  TTTTGACTTC  CTTGAATTAC  CTTGACGTGG  ACTTCTCTTC  TTCGATTGAC   1790
TTCTGCTGAA  TCATGAAGAA  CTTTTCTATG  ACAGGGACTA  AACATTATTA  AGGAGTCTTT   1850
TCGGTTGCGC  GGTCGTTGAA  GTCTAAAACA  CCTTTCGATA  GTTGACCGGA  CTTCTGTAAC   1910
AGAAAGGACG  TGAACTGTAA  GAAGCGGATA  GCTAATTCGT  AGGGTTACAC  TTACTCTTAA   1970
AGACGTTACT  TTTTCCTCTG  GTCAAGTCGT  CGGTAGAATA  GTTGGAAGAC  TTGGGGTTTC   2030
CTTTCGGTCG  TTTGGTCGAC  GAACGAGAAT  CCTGAAAAAC  GTTAACGAAA  CAATCAGTCC   2090
GTCCTGTTTT  CGAGTACTAC  AGGGTCTCCT  CAGTGACTAC  AGTGTACGTT  ATCTTGATTT   2150
TAGGCCCTCA  TTATTCTTGT  AAGTATAACG  AGACCGATGT  AACTGGAACT  TGATAAGACA   2210
AACAAAGGTA  TTTCTGGTAT  TGTAACTTCC  CTTTCGAGTT  ACGGAGAGTC  ATTAATCGTG   2270
TTAGAACCTT  CAACACGTTC  TGGATCTTCG  GTGCAAATCT  GAGGAACACC  GAGAACCCTG   2330
TGAATAGTCA  CTACTAAGTT  TACGATATGT  TAATCGGTTT  AGAAATCCAC  AACTAAGAGT   2390
TTATTTTTTC  ATACAGAGGC  ATAGTCTCGG  TCGATTTCAC  TCACTTACGA  CATCTGAACA   2450
GAATGTAAAC  GACATCGTCA  CCCCTTTTCT  GCGACTCCCC  AAAAGAAAAA  AACAAAACAA   2510
AACAAAACAA  AAAAAGGTGT  AAAATGTACT  GACTAACGTC  TAC                      2553
```

( 2 ) INFORMATION FOR SEQ ID NO:2:

( i ) SEQUENCE CHARACTERISTICS:
        ( A ) LENGTH: 325 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | His | Tyr | Met | Ser | Gly | His | Ser | Asn | Phe | Val | Ser | Tyr | Val | Cys | Ile |
|---|---|---|---|---|---|---|---|---|---|---|---|---|---|---|---|
| 1 | | | | 5 | | | | | 10 | | | | | 15 | |

| Ile | Pro | Ser | Ser | Asp | Ile | Tyr | Pro | His | Gly | Leu | Ile | Ala | Thr | Gly | Gly |
|---|---|---|---|---|---|---|---|---|---|---|---|---|---|---|---|
| | | | | 20 | | | | 25 | | | | | 30 | | |

| Asn | Asp | His | Asn | Ile | Cys | Ile | Phe | Ser | Leu | Asp | Ser | Pro | Met | Pro | Leu |
|---|---|---|---|---|---|---|---|---|---|---|---|---|---|---|---|
| | | 35 | | | | | 40 | | | | | 45 | | | |

| Tyr | Ile | Leu | Lys | Gly | His | Lys | Asp | Thr | Val | Cys | Ser | Leu | Ser | Ser | Gly |
|---|---|---|---|---|---|---|---|---|---|---|---|---|---|---|---|
| | 50 | | | | | 55 | | | | | 60 | | | | |

| Lys | Phe | Gly | Thr | Leu | Leu | Ser | Gly | Ser | Trp | Asp | Thr | Thr | Ala | Lys | Val |
|---|---|---|---|---|---|---|---|---|---|---|---|---|---|---|---|
| 65 | | | | | 70 | | | | | 75 | | | | | 80 |

| Trp | Leu | Asn | Asp | Lys | Cys | Met | Met | Thr | Leu | Gln | Gly | His | Thr | Ala | Ala |
|---|---|---|---|---|---|---|---|---|---|---|---|---|---|---|---|
| | | | | 85 | | | | | 90 | | | | | 95 | |

Val Trp Ala Val Lys Ile Leu Pro Glu Gln Gly Leu Met Leu Thr Gly
            100                 105                 110

Ser Ala Asp Lys Thr Ile Lys Leu Trp Lys Ala Gly Arg Cys Glu Arg
            115                 120                 125

Thr Phe Leu Gly His Glu Asp Cys Val Arg Gly Leu Ala Ile Leu Ser
            130                 135                 140

Glu Thr Glu Phe Leu Ser Cys Ala Asn Asp Ala Ser Ile Arg Arg Trp
145                     150                 155                 160

Gln Ile Thr Gly Glu Cys Leu Glu Val Tyr Phe Gly His Thr Asn Tyr
                165                 170                 175

Ile Tyr Ser Ile Ser Val Phe Pro Asn Ser Lys Asp Phe Val Thr Thr
            180                 185                 190

Ala Glu Asp Arg Ser Leu Arg Ile Trp Lys His Gly Glu Cys Ala Gln
            195                 200                 205

Thr Ile Arg Leu Pro Ala Gln Ser Ile Trp Cys Cys Cys Val Leu Glu
    210                 215                 220

Asn Gly Asp Ile Val Val Gly Ala Ser Asp Gly Ile Ile Arg Val Phe
225                 230                 235                 240

Thr Glu Ser Glu Glu Arg Thr Ala Ser Ala Glu Glu Ile Lys Ala Ser
                245                 250                 255

Leu Ser Arg Glu Ser Pro Leu Ile Ala Lys Val Leu Thr Thr Glu Pro
            260                 265                 270

Pro Ile Ile Thr Pro Val Arg Arg Thr Leu Pro Cys Arg Val Thr Arg
        275                 280                 285

Ser Met Ile Ser Ser Cys Leu Ser Arg Leu Val Ser Thr Ser Leu Ser
        290                 295                 300

Thr Ser Asp Ser His Leu Thr Ile Thr Ala Leu His Leu Phe Leu Thr
305                 310                 315                 320

Thr Thr Thr Thr Glu
                325

( 2 ) INFORMATION FOR SEQ ID NO:3:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Gly Ile Gly Ala Val Leu Lys Val Leu Thr Thr Gly Leu Pro Ala Leu
1                   5                   10                  15

Ile Ser Trp Ile Lys Arg Lys Arg Gln Gln
                20                  25

( 2 ) INFORMATION FOR SEQ ID NO:4:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Cys Leu Glu Val Tyr Phe Gly His Thr Asn Tyr Ile Tyr Ser Ile Ser
1                   5                   10                  15

```
Val  Phe  Pro  Asn  Ser  Lys  Asp  Phe  Val  Thr
               20                      25
```

( 2 ) INFORMATION FOR SEQ ID NO:5:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Leu  Glu  Val  Tyr  Phe  Gly  His  Thr  Asn  Tyr  Ile  Tyr  Ser  Ile  Ser  Val
1                   5                    10                       15
Phe  Pro  Asn  Ser  Lys  Asp  Phe  Val  Thr  Thr
               20                      25
```

( 2 ) INFORMATION FOR SEQ ID NO:6:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Glu  Gln  Gly  Leu  Met  Leu  Thr  Gly  Ser  Ala  Asp  Lys  Thr  Ile  Lys  Leu
1                   5                    10                       15
Trp  Lys  Ala  Gly  Arg  Cys  Glu  Arg  Thr  Phe
               20                      25
```

( 2 ) INFORMATION FOR SEQ ID NO:7:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Phe  Leu  Gly  His  Glu  Asp  Cys  Val  Arg  Gly  Leu  Ala  Ile  Leu  Ser  Glu
1                   5                    10                       15
Thr  Glu  Phe  Leu  Ser  Cys  Ala  Asn  Asp  Ala
               20                      25
```

( 2 ) INFORMATION FOR SEQ ID NO:8:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Lys  Val  Leu  Thr  Thr  Glu  Pro  Pro  Ile  Ile  Thr  Pro  Val  Arg
1                   5                    10
```

( 2 ) INFORMATION FOR SEQ ID NO:9:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:9:

Lys Val Leu Thr Thr Glu Pro Pro Ile Ile
1               5                   10

( 2 ) INFORMATION FOR SEQ ID NO:10:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:10:

Thr Thr Glu Pro Pro Ile Ile Thr Pro Val Arg
1               5                   10

( 2 ) INFORMATION FOR SEQ ID NO:11:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:11:

Lys Val Leu Thr Thr Glu Pro Pro Ile
1               5

( 2 ) INFORMATION FOR SEQ ID NO:12:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:12:

Lys Val Leu Thr Thr Glu Pro Pro
1               5

( 2 ) INFORMATION FOR SEQ ID NO:13:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:13:

Lys Val Leu Thr Thr Glu
1               5

( 2 ) INFORMATION FOR SEQ ID NO:14:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:14:

Val Leu Thr Thr Glu Pro Pro Ile Ile Thr Pro Val
1               5                   10

( 2 ) INFORMATION FOR SEQ ID NO:15:

( i ) SEQUENCE CHARACTERISTICS:
  ( A ) LENGTH: 13 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:15:

Val Leu Thr Thr Glu Pro Pro Ile Ile Thr Pro Val Arg
1               5                   10

( 2 ) INFORMATION FOR SEQ ID NO:16:

( i ) SEQUENCE CHARACTERISTICS:
  ( A ) LENGTH: 13 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:16:

Val Leu Thr Thr Glu Pro Pro Ile Ile Thr Pro Val Arg
1               5                   10

( 2 ) INFORMATION FOR SEQ ID NO:17:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: cDNA ( i v ) ANTI-SENSE: YES ( x i ) SEQUENCE DESCRIPTION: SEQ ID NO:17:

CACTATATGA GCGGCCACTC TAATT                                25